US006314201B1

(12) United States Patent
Roder

(10) Patent No.: US 6,314,201 B1
(45) Date of Patent: Nov. 6, 2001

(54) AUTOMATIC X-RAY DETERMINATION OF SOLDER JOINT AND VIEW DELTA Z VALUES FROM A LASER MAPPED REFERENCE SURFACE FOR CIRCUIT BOARD INSPECTION USING X-RAY LAMINOGRAPHY

(75) Inventor: Paul A. Roder, Fort Collins, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/174,513

(22) Filed: Oct. 16, 1998

(51) Int. Cl.⁷ ........................................................ G06K 9/00

(52) U.S. Cl. ........................... 382/147; 382/106; 382/151

(58) Field of Search .................................... 382/147, 141, 382/143, 144, 145, 146, 148, 149, 150, 151, 154, 106, 199; 348/86, 87, 125, 126; 702/57, 58, 59

(56) References Cited

U.S. PATENT DOCUMENTS

| 4,614,430 | 9/1986 | Hara et al. . |
|---|---|---|
| 4,677,473 | 6/1987 | Okamoto et al. . |
| 4,707,734 | 11/1987 | Labinger et al. . |
| 4,809,308 | 2/1989 | Adams et al. . |
| 4,852,131 | 7/1989 | Armistead . |
| 4,926,452 | 5/1990 | Baker et al. . |
| 4,942,618 * | 7/1990 | Sumi et al. ............................ 382/154 |
| 5,081,656 | 1/1992 | Baker et al. . |
| 5,097,492 | 3/1992 | Baker et al. . |
| 5,164,994 | 11/1992 | Bushroe . |
| 5,199,054 | 3/1993 | Adams et al. . |
| 5,259,012 | 11/1993 | Baker et al. . |
| 5,291,535 | 3/1994 | Baker e tal. . |
| 5,465,152 | 11/1995 | Bilodeau et al. . |
| 5,500,886 | 3/1996 | Duff . |
| 5,561,696 | 10/1996 | Adams et al. . |
| 5,583,904 | 12/1996 | Adams . |
| 5,592,562 | 1/1997 | Rooks . |
| 5,621,811 | 4/1997 | Roder et al. . |
| 5,687,209 | 11/1997 | Adams . |
| 5,694,487 * | 12/1997 | Lee ....................................... 382/201 |

FOREIGN PATENT DOCUMENTS 0 683 389   11/1995   (EP) .

OTHER PUBLICATIONS

Hasenkamp, "Radiographic Laminography," *Materials Evaluation*, Aug. 1974, pp. 169–180.

Blanche, "Nondestructive Testing Techniques for Multilayer Printed Wiring Boards," Nondestructive Testing: Trends and Techniques, NASA SP–5082, Oct. 1968, pp. 1–13.

Hamre, "Nondestructive Testing Techniques for Multilayer Printed Wiring Boards," Report No. IITRI–E6024–15, Sep. 1965.

Deane et al., IRT Corp., "Using X–Ray Vision to Verify SMD–Board Quality," *Electronics Test*, Feb. 1987, pp. 32–35.

Soron, IRT Corp., X–Ray Inspection Meets Increased PWB Throughput, Density Challenge–Part 1, *Electronics*, Oct. 1987, pp. 36–37.

(List continued on next page.)

Primary Examiner—Joseph Mancuso
Assistant Examiner—Vikkram Bali

(57) ABSTRACT

An improved circuit board inspection system incorporates self learning techniques for accurate determination of Z-axis elevations of electrical connections. A Delta Z, referenced to a laser range finder generated surface map of the circuit board, is automatically determined from a series of cross sectional images of the electrical connections for each electrical connection on the circuit board. The Delta Z values for each electrical connection are stored in a data base from which customized Delta Z values for specifically defined board views may be calculated.

27 Claims, 15 Drawing Sheets

OTHER PUBLICATIONS

Pound, "Image Processing Boosts the Power of Non-destructive Testing," *Electronic Packaging and Production*, Jun. 1985.

Casey, "X–Ray Inspection," *Manufacturing Systems*, Jul. 1987, p. 18ff.

Corey, IRT Corp., "Artificial Perception Gives Super Vision," *Research and Development*, Oct. 1984.

LaClair, "Nondestructive Measurement and Inspection Process," IBM Technical Disclosure Bulletin, vol. 18, No. 12, May 1976.

Hufault et al., "Lead–Indium Solder Joint Analysis," IBM Technical Disclosure Bulletin, vol. 19, No. 11, Apr. 1977.

Wittenberg, "IRT Improves SMT X–Ray Inspection System," *Electronic Engineering Times*, Oct. 5, 1987, p. 53.

Phelps, Christi "Four Pi Captures Contact, Capital; Unveils Product," *San Diego Business Journal*, Week of Oct. 10–16, 1888.

Four Pi Systems product brochure for "3DX Series 2000" Automated Inspection System, Copyright 1988.

Juha, Mike, "Automated Inspection of Surface Mounted Device Solder Connections", *Proceedings of Soldering Technology Seminar–Feb. 19–20, 1985*, Naval Weapons.

D. Meyer–Ebrecht and H. Weiss, "Tomosynthesis—3–D X–ray imaging by means of holography or elctronics", *OPTICA ACTA*, vol. 24, No. 4, 1977, pp. 293–303.

Kolitsi et al., "A multiple projection method for digital tomosynthesis", *Med. Phys.*, vol. 19, No. 4, Jul./Aug. 1992, pp. 1045–1050.

Haaker et al., "Digital angiographic tomosynthesis with fewer artifacts", *Med. Phys.*, vol. 12, No. 4, Jul./Aug. 1985, pp. 431–436.

Kruger et al., "Reconstruction of blood vessels from x–ray subtraction projections: Limited angle geometry", *Med. Phys.*, vol. 14, No. 6, Nov./Dec. 1987, pp. 940–948.

Baranov et al., "System of Digital Tomosynthesis for Nondestructive Testing", *Plenum Publishing Corporation 0038–5492/88/2405*, 1989, pp. 321–327.

Vainberg et al., "Reconstruction of the Internal Three–Dimensional Structure of Objects Based on Real–Time Integral Projections", *Plenum Publishing Corporation 0038–5492/81/1706*, 1982, pp. 415–423.

Kang et al., "A New X–ray Cross–Sectional Imaging System for Arbitrary Angle Inspection of BGA Package", *Proceedings of the Technical Program–NEPCON® East '97–Jun. 9–12, 1997, Boston, Massachusetts, pp. 109–119*.

* cited by examiner

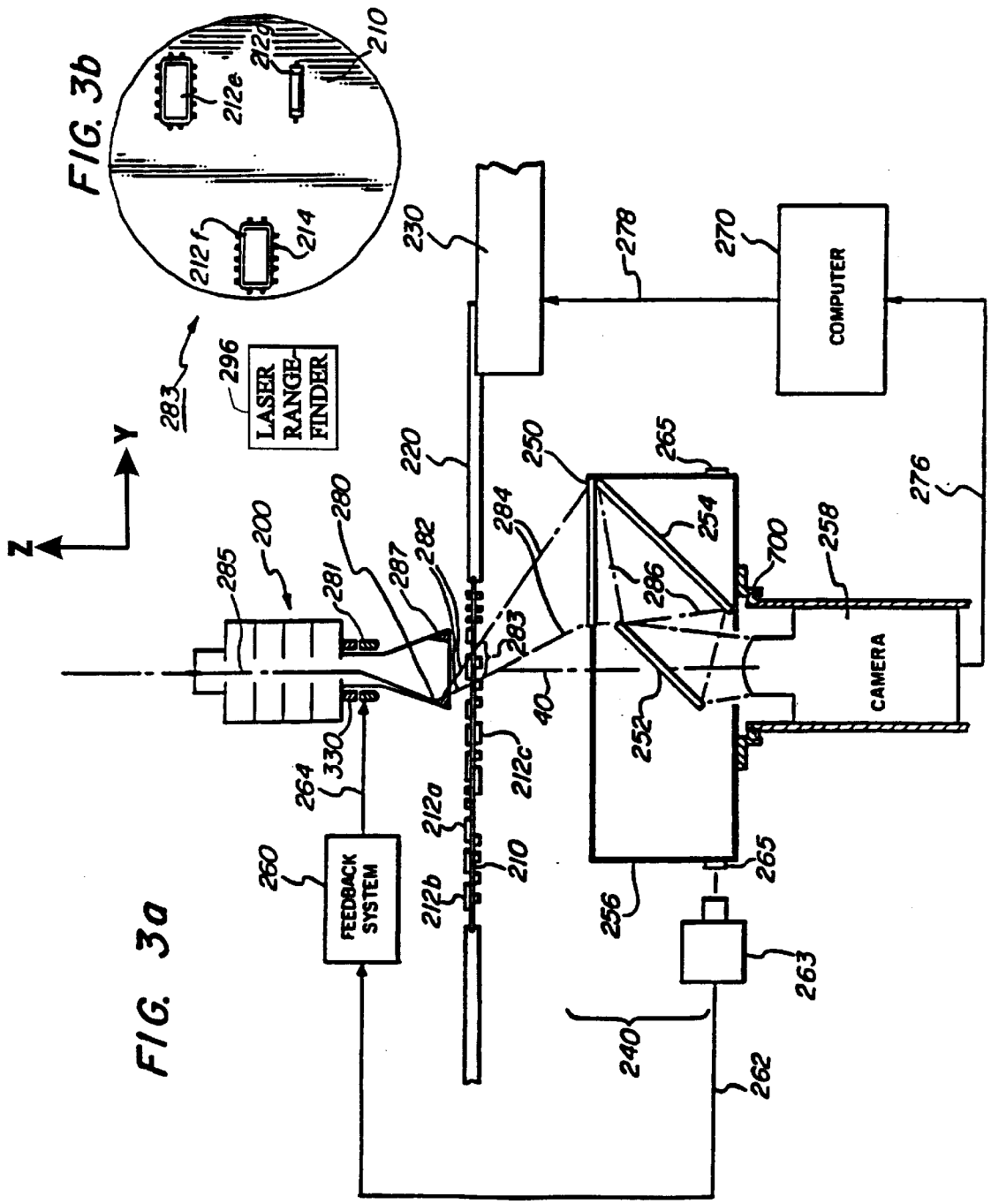

AUTOMATIC X-RAY DETERMINATION OF SOLDER JOINT AND VIEW DELTA Z VALUES FROM A LASER MAPPED REFERENCE SURFACE FOR CIRCUIT BOARD INSPECTION USING X-RAY LAMINOGRAPHY

FIELD OF THE INVENTION

The invention relates generally to the rapid, high resolution inspection of circuit boards using a computerized laminography system, and in particular, to systems which automatically determine the relative distance between a solder joint elevation and a circuit board surface elevation using a laminographic image of the solder joint and a surface map of the circuit board.

BACKGROUND OF THE INVENTION

Rapid and precise quality control inspections of the soldering and assembly of electronic devices have become priority items in the electronics manufacturing industry. The reduced size of components and solder connections, the resulting increased density of components on circuit boards and the advent of surface mount technology (SMT), which places solder connections underneath device packages where they are hidden from view, have made rapid and precise inspections of electronic devices and the electrical connections between devices very difficult to perform in a manufacturing environment.

Many existing inspection systems for electronic devices and connections make use of penetrating radiation to form images which exhibit features representative of the internal structure of the devices and connections. These systems often utilize conventional radiographic techniques wherein the penetrating radiation comprises X-rays. Medical X-ray pictures of various parts of the human body, e.g., the chest, arms, legs, spine, etc., are perhaps the most familiar examples of conventional radiographic images. The images or pictures formed represent the X-ray shadow cast by an object being inspected when it is illuminated by a beam of X-rays. The X-ray shadow is detected and recorded by an X-ray sensitive material such as film or other suitable means.

The appearance of the X-ray shadow or radiograph is determined not only by the internal structural characteristics of the object, but also by the direction from which the incident X-rays strike the object. Therefore, a complete interpretation and analysis of X-ray shadow images, whether performed visually by a person or numerically by a computer, often requires that certain assumptions be made regarding the characteristics of the object and its orientation with respect to the X-ray beam. For example, it is often necessary to make specific assumptions regarding the shape, internal structure, etc. of the object and the direction of the incident X-rays upon the object. Based on these assumptions, features of the X-ray image may be analyzed to determine the location, size, shape, etc., of the corresponding structural characteristic of the object, e.g., a defect in a solder connection, which produced the image feature. These assumptions often create ambiguities which degrade the reliability of the interpretation of the images and the decisions based upon the analysis of the X-ray shadow images. One of the primary ambiguities resulting from the use of such assumptions in the analysis of conventional radiographs is that small variations of a structural characteristic within an object, such as the shape, density and size of a defect within a solder connection, are often masked by the overshadowing mass of the solder connection itself as well as by neighboring solder connections, electronic devices, circuit boards and other objects. Since the overshadowing mass and neighboring objects are usually different for each solder joint, it is extremely cumbersome and often nearly impossible to make enough assumptions to precisely determine shapes, sizes and locations of solder defects within individual solder joints.

In an attempt to compensate for these shortcomings, some systems incorporate the capability of viewing the object from a plurality of angles. The additional views enable these systems to partially resolve the ambiguities present in the X-ray shadow projection images. However, utilization of multiple viewing angles necessitates a complicated mechanical handling system, often requiring as many as five independent, non-orthogonal axes of motion. This degree of mechanical complication leads to increased expense, increased size and weight, longer inspection times, reduced throughput, impaired positioning precision due to the mechanical complications, and calibration and computer control complications due to the non-orthogonality of the axes of motion.

Many of the problems associated with the conventional radiography techniques discussed above may be alleviated by producing cross-sectional images of the object being inspected. Tomographic techniques such as laminography and computed tomography (CT) have been used in medical applications to produce cross-sectional or body section images. In medical applications, these techniques have met with widespread success, largely because relatively low resolution on the order of one or two millimeters (0.04 to 0.08 inches) is satisfactory and because speed and throughput requirements are not as severe as the corresponding industrial requirements.

In the case of electronics inspection, and more particularly, for inspection of electrical connections such as solder joints, image resolution on the order of several micrometers, for example, 20 micrometers (0.0008 inches) is preferred. Furthermore, an industrial solder joint inspection system must generate multiple images per second in order to be practical for use on an industrial production line. Laminography systems which are capable of achieving the speed and accuracy requirements necessary for electronics inspection are described in the following patents: 1) U.S. Pat. No. 4,926,452 entitled "AUTOMATED LAMINOGRAPHY SYSTEM FOR INSPECTION OF ELECTRONICS", issued to Baker et al.; 2) U.S. Pat. No. 5,097,492 entitled "AUTOMATED LAMINOGRAPHY SYSTEM FOR INSPECTION OF ELECTRONICS", issued to Baker et al.; 3) U.S. Pat. No. 5,081,656 entitled "AUTOMATED LAMINOGRAPHY SYSTEM FOR INSPECTION OF ELECTRONICS", issued to Baker et al.; 4) U.S. Pat. No. 5,291,535 entitled "METHOD AND APPARATUS FOR DETECTING EXCESS/INSUFFICIENT SOLDER DEFECTS", issued to Baker et al.; 5) U.S. Pat. No. 5,621,811 entitled "LEARNING METHOD AND APPARATUS FOR DETECTING AND CONTROLLING SOLDER DEFECTS", issued to Roder et al.; 6) U.S. Pat. No. 5,561,696 "METHOD & APPARATUS FOR INSPECTING ELECTRICAL CONNECTIONS", issued to Adams et al.; 7) U.S. Pat. No. 5,199,054 entitled "METHOD AND APPARATUS FOR HIGH RESOLUTION INSPECTION OF ELECTRONIC ITEMS", issued to Adams et al.; 8) U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al.; 9) U.S. Pat. No. 5,583,904 entitled "CONTINUOUS LINEAR SCAN LAMINOGRAPHY SYSTEM AND METHOD", issued to Adams; and 10) U.S. Pat. No. 5,687,209 entitled "AUTOMATIC WARP COMPENSATION FOR LAMINOGRAPHIC CIRCUIT BOARD INSPECTION", issued to Adams. The entirety of each of the above referenced patents is hereby incorporated herein by reference.

In a laminography system which views a fixed object and has an imaging area which is smaller than the object being inspected, it may be necessary to move the object around to position different regions of the object within the imaging area thus generating multiple laminographs which, when pieced together form an image of the entire object. This is frequently achieved by supporting the object on a mechanical handling system, such as an X,Y,Z positioning table. The table is then moved to bring the desired regions of the object into the imaging area. Movement in the X and Y directions locates the region to be examined, while movement in the Z direction moves the object up and down to select the plane within the object where the cross sectional image is to be taken.

Several of the above referenced patents disclose devices and methods for the generation of cross-sectional images of test objects at a fixed or selectable cross-sectional image focal plane. In these systems, an X-ray source system and an X-Ray detector system are separated in the "Z" axis direction by a fixed distance and the cross-sectional image focal plane is located at a predetermined specific position in the "Z" axis direction which is intermediate the positions of the X-ray source system and the X-ray detector system along the "Z" axis. The X-Ray detector system collects data from which a cross-sectional image of features in the test object, located at the cross-sectional image focal plane, can be formed. All of these systems postulate that the features desired to be imaged are located in the fixed or selectable cross-sectional image focal plane at the predetermined specific position along the "Z" axis. Thus, in these systems, it is essential that the positions of the cross-sectional image focal plane and the plane within the object which is desired to be imaged, be configured to coincide at the same position along the "Z" axis. If this condition is not met, then the desired image of the selected feature within the test object will not be acquired. Instead, a cross-sectional image of a plane within the test object which is either above or below the plane which includes the selected feature will be acquired.

Presently, one technique commonly used for positioning the selected feature of the test object within the cross-sectional image focal plane physically measures the "Z" axis position of the selected feature. Using this measurement, the test object is then positioned along the "Z" axis such that the selected feature coincides with the "Z" axis position of the cross-sectional image focal plane. Any of a variety of standard methods and instruments may be used to physically measure the "Z" axis position of the selected feature of the test object. There are several types of commercially available Z-ranging systems which are used to determine the distance between a known location in "Z" and a feature on the surface, or just below the surface, of the test object. Such systems are as simple as mechanical fixturing of the test object, a mechanical probe, a laser based optical triangulation system, an optical interferometric system, an ultrasonic system, or any other type of measuration device that is suitable. Any one of these "Z" distance measuring systems is typically used to form a "Z-map" of the surface of the test object. The Z-map typically consists of an X and Y array of the Z-values of the surface of the test object. The (X,Y) locations being points on a plane of the test object which is substantially parallel to the cross-sectional image focal plane. The systems most commonly used in systems for cross-sectional image formation of features on circuit boards have been laser based triangulation range finders.

Range finders have been used in particular for cross-sectional X-ray image systems that are used to image electronic circuit board assemblies. Circuit board assemblies are typically very thin in comparison to the surface area in which the components are mounted. Some circuit assemblies are made with very dimensionally stable material, such as ceramic substrates. However, the majority of circuit board assemblies are constructed with board material that is somewhat flexible or in some cases very flexible. This flexibility allows the board to develop a warp in the axis perpendicular to the major surface areas. Additionally, some circuit board assemblies have variations in board thickness. Besides electronic assemblies, there are many other objects that have dimensional variation on a scale that is significant when compared to the depth of field of the "Z" focal plane in cross-sectional X-ray imaging. By measuring the surface of a warped test object, means can then often be used to properly adjust the positional relationship of the test object with respect to the "Z" focal plane of the cross-sectional imaging system so that the desired image of the features of interest within the test object can be imaged.

Specifically, one such range finder system is designed for use in a system such as that described in U.S. Pat. No. 4,926,452 to Baker, et al. Baker et al. discloses a laminography system in which an X-ray based imaging system having a very shallow depth of field is used to examine solid objects such as printed circuit cards. The shallow depth of field provides a means for examining the integrity of a solder joint without interference from the components above and below the solder joint. The material above and below the solder joint is out of focus, and hence, contributes to a more or less uniform background. To provide the needed selectivity, the depth of field of the laminographic imaging system is on the order of less than approximately 2 mils. Unfortunately, surface variations on the printed circuit card often exceed this tolerance. To overcome this drawback, the surface of the printed circuit card is mapped using a laser range finder. The detailed laser range finder map is then used to position the circuit card with respect to the X-ray imaging system such that the component of interest is in focus even when the card is translated from one field of interest to another.

One disadvantage of most laser ranging systems is that they require that the surface being mapped be free of imperfections which can interfere with the laser beam. Two types of commercially available ranging systems are often used. Both types operate by illuminating a point on the surface with a collimated beam of light from a laser. In the first type of system, the laser beam strikes the surface at right angles to the surface and illuminates a small spot on the surface. The illuminated spot is imaged onto an array of detectors by a lens. The distance from the laser to the surface determines the degree to which the illuminated spot is displaced from the axis of the lens. As a result, as the distance changes, the image of the spot moves along the array of detectors. The identity of the detector on which the projected spot falls provides the information needed to determine the distance to the point on the surface. In this type of system, imperfections on the surface can interfere with the laser beam at the point of measurement resulting in substantial errors in the measurement. In more sophisticated versions of this type of system, the image of the laser spot falls on more than one detector. The detection circuitry computes the center of the image to provide a more precise distance determination. Here, imperfections in the surface that distort the image on the detector array will also cause errors even though the height of the imperfection is insufficient to cause a significant distance error. The second type of system assumes that the surface is flat and reflective. In this type of system, the laser beam is directed at the surface of the circuit board at an oblique angle and reflected from the surface onto the detector array without an imaging lens. The distance is then measured by identifying the detector receiving the reflected light beam. The distance measurement relies on a knowledge of the angle of incidence of the laser beam with respect to the surface. If the surface includes an imperfection which has dimensions similar to that of the laser beam, this assumption will not be satisfied, since the surface of the imperfection will determine the angle of incidence. The resulting errors can be much larger than the height of the imperfection in this type of system. In principle, the problems introduced by such imperfections could be mitigated by increasing the diameter of the laser beam. Unfortunately, the diameter of the laser beam must be kept to a minimum to provide the required accuracy in the range measurement. Laser range finding measurements are also made using a CCD camera which views the surface and an image analyzer which analyzes the image acquired by the CCD camera.

Another disadvantage of existing Z-map systems is the possibility that the desired features to be measured are not in strict mechanical relationship to the Z-map surface of the test object. This can occur, for example, when the desired feature to be imaged is on the opposite side from the Z-map surface, of a double-sided circuit board assembly that has a significant variation in board thickness. To compensate for this effect, existing cross-sectional imaging systems would have to generate a Z-map of both sides of a test object at added time and complexity. There is also the possibility that the feature to be imaged in the test object is internal to the test object at a Z distance from the Z-map surface of the board, with significant variation in this distance from board to board or within the same board. Additionally, warpage of the circuit board may not be adequately measured by the Z-map of the surface of the board.

For solder joint inspections, some of the inaccuracies inherent in laser created Z-maps of the surface of a circuit board are partially compensated for by measuring "Delta Z" values. Delta Z values are intended to represent the distance between the actual Z elevations of the solder pads and the Z elevation values determined via the laser readings. Currently, laser surface map points are each given a Delta Z value through a tedious and error prone method. This involves the user attempting to manually focus on a feature which is near the laser surface map point and determining the Z elevation of that feature. Delta Z is then defined as the difference between the user determined Z elevation and the laser determined Z elevation for that location. In many cases, it may be necessary for the user to repeat this process for numerous locations on the circuit board. There are several significant problems with this approach, including the following. A) The manual focus technique is subjective and error prone. B) There must be something suitable for the user to focus on near the laser map point. Frequently there is not, so the user will migrate far from the laser map point to find something to focus on, yielding an inaccurate Delta Z value. C) The assumption is often made that the circuit board is perfectly flat within the triangles formed by the laser map points. Frequently, it is difficult to supply enough points in certain areas to accurately model warpage of the circuit board. D) There is no way in this method to handle consistent variations in circuit board thickness. For example, many circuit boards have certain areas which are typically thicker than other areas of the board. E) There is no way to map the bottom of the circuit board since there is no bottom laser.

In summary, accurate inspection of a solder joint using a cross-sectional image(s) of the solder joint requires that the vertical position, i.e., Z-axis location, within the solder joint at which the cross-sectional image(s) is to be acquired be accurately known. The surface of the circuit board on which the solder joint is located often provides a convenient reference plane from which vertical positions within the solder joint may be determined. Presently, laser range finding technology is often used to create a surface map of the circuit board. However, due to a variety of factors, several of which are discussed above, the laser determined Z values do not permit accurate determination of the actual Z-axis locations of the solder joints being inspected.

The present invention provides improvements which address the above listed specific problems. Particularly important is that it both removes the tedious and error prone method of manually setting laser Delta Z values, while supplying correct Z values for each board view in cases where board warpage is consistent within the surface map triangles.

Several advantages of the present invention include: ease of use; improved accuracy of Z elevation determination; ability to handle consistent board thickness variations in certain areas of the circuit board; and ability to model board warpage more accurately. Additionally, since the present invention is compatible with the currently used manual technique, it can be used on an as needed basis. Thus, it is possible to use the old manually set Delta Z values in cases where it is not desired to use the new method.

Accordingly, one object of the present invention is to improve the accuracy of the Z-map systems used in the prior art, for example, laser range finding systems, with a system that automatically compensates for test object warpage without requiring additional system hardware over that hardware which is required to form the X-ray laminographic cross-sectional image.

Another object and advantage of the present invention is that it provides an improved way to produce high resolution cross sectional images of electrical connections.

SUMMARY OF THE INVENTION

As used throughout, the phrase "board view" refers to an image of a particular region or area of a circuit board identified by a specific x,y coordinate of the circuit board. Since the area imaged by a typical laminograpy system is smaller than a typical circuit board, each "board view" includes only a portion of the circuit board. Thus, the circuit board is generally moved around to different positions thereby placing different regions of the circuit board within the imaging area of the system. A complete inspection of a circuit board includes multiple "board views", i.e., laminographic images, which, if pieced together would form an image of the entire circuit board or selected regions of the circuit board requiring inspection.

The present invention comprises a greatly improved computerized laminography system which provides more accurate determination of the Z elevations of solder joints to be inspected.

The present invention includes a technique for automatically learning a Delta Z value for every solder joint on a circuit board during initial board setup. This is done through an automatic analysis of X-ray image focus or other image quality parameter. The machine creates multiple laminographic image slices through the approximate board surface and determines the Z elevation of every solder joint relative to a surface map of the board.

After each joint Delta Z is determined, a program then calculates a Delta Z for each board view using all of the joint Delta Z values within that board view. There are several ways this can be done, such as averaging, or throwing out outliers, etc. This method is also extensible to actually determine that within a particular board view, board warpage is such that some joints may require a different slice within the board view.

All of the joint Delta Z values are stored before calculating a Delta Z value for the board view which includes those joints. This is advantageous in case minor CAD changes change the locations of the board views. Since the Delta Z for each joint has already been measured and saved, it is a simple matter to recalculate a new Delta Z value for the new board view using the new board view joint lists and the stored Delta Z values for the joints located within the new board view.

In a first aspect, the present invention is a device for inspecting electrical connections on a circuit board comprising: a source of X-rays which emits X-rays through the electrical connection from a plurality of positions; an X-ray detector system positioned to receive the X-rays produced by the source of X-rays which have penetrated the electrical connection, the X-ray detector system further comprising an output which emits data signals corresponding to an X-ray image of the electrical connection produced by the X-rays received and detected by the X-ray detector after penetrating the electrical connection; an image memory which combines the detector data signals to form an image database which contains information sufficient to form a cross-sectional image of a cutting plane of the electrical connection at an image plane; and a processor which controls the acquisition of the cross-sectional image and analyzes the cross-sectional image, the image processor further comprising: a Z-axis controller for varying a Delta Z value, i.e., the Z-axis distance between the image plane and a reference Z-axis position, and acquiring a plurality of Delta Z images of the electrical connection at a plurality of the Delta Z values; an image gradient section which calculates and stores a plurality of gradients for each of the plurality of Delta Z images; a variance calculator section which determines a variance of the plurality of gradients for each of the plurality of Delta Z images; and a comparator which compares the variances of the gradients for each of the plurality of Delta Z images. The device may further include a surface mapper for creating a surface map of the circuit board. In some configurations, the surface mapper further comprises a laser range finder for determining reference Z-axis values for a plurality of points on the circuit board thereby creating a laser surface map of the circuit board. The image gradient may be approximated over a K×K pixel grid by the following relation:

$$G_{MR}[f(x,y)] \approx |f(x-N,y-N)-f(x+M,y+M)| + |f(x+M,y-N)-f(x-N,y+M)|$$

where $f(x,y)$ represents a gray value of a pixel located at $x,y$; K is an integer which is greater than or equal to 2; $N=(K-1)/2$ rounded down to the nearest integer; and $M=K-N-1$. In some configurations, the comparator further comprises means for fitting the variances of the plurality of gradients for each of the plurality of Delta Z images with either one of a parabolic curve or a Gaussian curve. Additionally, the comparator may further comprise means for determining a Delta Z value corresponding to a maximum value of the parabolic curve or the Gaussian curve. In some configurations, the source of X-rays comprises a plurality of X-ray sources and the X-ray detector system comprises a plurality of X-ray detectors. The processor may further comprise an image section which produces the cross-sectional image of a cutting plane of the electrical connection from the image database.

A second aspect of the present invention is a method of determining the Z-axis position of an electrical connection on a circuit board comprising the steps of: determining a reference Z-axis position, $Z_{RF}$; acquiring a first cross sectional image of the electrical connection at a first Z-axis position, $Z_{RF}+\Delta Z_1$, and a second cross sectional image of the electrical connection at a second Z-axis position, $Z_{RF}+\Delta Z_2$; determining a first plurality of gradients for the first cross sectional image and a second plurality of gradients for the second cross sectional image; calculating a first variance for the first plurality of gradients corresponding to the first cross sectional image at the first Z-axis position, $Z_{RF}+\Delta Z_1$, and a second variance for the second plurality of gradients corresponding to the second cross sectional image at the second Z-axis position, $Z_{RF}+\Delta Z_2$; and analyzing the first and second variances and deriving therefrom the Z-axis position of the electrical connection. In certain configurations, the reference Z-axis position is determined with a range finder which may further include a laser range finder.

A third aspect of the present invention includes a method of determining the Z-axis position of an electrical connection on a circuit board comprising the steps of: determining a reference Z-axis position, $Z_{RF}$; acquiring a first cross sectional image of the electrical connection at a first Z-axis position, $Z_{RF}+\Delta Z_1$, a second cross sectional image of the electrical connection at a second Z-axis position, $Z_{RF}+\Delta Z_2$, and a third cross sectional image of the electrical connection at a third Z-axis position, $Z_{RF}+\Delta Z_3$; determining a first plurality of gradients for the first cross sectional image, a second plurality of gradients for the second cross sectional image and a third plurality of gradients for the third cross sectional image; calculating a first variance for the first plurality of gradients corresponding to the first cross sectional image at the first Z-axis position, $Z_{RF}+\Delta Z_1$, a second variance for the second plurality of gradients corresponding to the second cross sectional image at the second Z-axis position, $Z_{RF}+\Delta Z_2$, and third variance for the third plurality of gradients corresponding to the third cross sectional image at the third Z-axis position, $Z_{RF}+\Delta Z_3$; and determining a maximum variance value derived from the first, second and third variances and selecting a corresponding Z-axis position, $Z_{RF}+\Delta Z_{MAX}$, corresponding to the maximum variance value, as the Z-axis position of the electrical connection. The method may further include the step of determining a mathematical function which includes points which approximate the values of the first, second and third variances. In some cases, the mathematical function is a parabola, while in other cases the mathematical function is a Gaussian. This aspect of the invention may further include a surface mapper for creating a surface map of the circuit board.

In a fourth aspect, the present invention is a device for inspecting electrical connections on a circuit board comprising: means for determining a reference Z-axis position, $Z_{RF}$; means for acquiring a first cross sectional image of the electrical connection at a first Z-axis position, $Z_{RF}+\Delta Z_1$, a second cross sectional image of the electrical connection at a second Z-axis position, $Z_{RF}+\Delta Z_2$, and a third cross sectional image of the electrical connection at a third Z-axis position, $Z_{RF}+\Delta Z_3$; means for determining a first plurality of gradients for the first cross sectional image, a second plurality of gradients for the second cross sectional image and a third plurality of gradients for the third cross sectional image; means for calculating a first variance for the first plurality of gradients corresponding to the first cross sectional image at the first Z-axis position, $Z_{RF}+\Delta Z_1$, a second variance for the second plurality of gradients corresponding to the second cross sectional image at the second Z-axis position, $Z_{RF}+\Delta Z_2$, and third variance for the third plurality of gradients corresponding to the third cross sectional image at the third Z-axis position, $Z_{RF}+\Delta Z_3$; and means for determining a maximum variance value derived from the first, second and third variances and selecting a corresponding Z-axis position, $Z_{RF}+\Delta Z_{MAX}$, corresponding to the maximum variance value, as the Z-axis position of the electrical connection. This device may further include means for determining a mathematical function which includes points which approximate the values of the first, second and third variances wherein the Z-axis position, $Z_{RF}+\Delta Z_{MAX}$, corresponding to the maximum variance value equals a Z-axis position which corresponds to a maximum value of the mathematical function. The mathematical function may be one of a parabola or a Gaussian. In some configurations, the means for determining the reference Z-axis position further comprises a laser range finder.

In a fifth aspect, the invention includes a method for inspecting electrical connections on a circuit board comprising the steps of: determining a Z-axis position for substantially all of the electrical connections on the circuit board; storing the Z-axis positions for substantially all of the electrical connections on the circuit board in a data base; selecting a first board view which includes a first portion of the circuit board; and deriving from the stored values of the Z-axis positions for the electrical connections included within the first board view, a Z-axis position for the first board view. The method may further include the step of creating a surface map of the circuit board with a range finder. In some configurations, the method further includes the steps of: selecting a second board view which includes a second portion of the circuit board; and deriving from the stored values of the Z-axis positions for the electrical connections included within the second board view, a Z-axis position for the second board view.

In a sixth aspect, the invention is a method for determining the Z-axis position of an electrical connection on a circuit board comprising the steps of: acquiring two or more cross sectional images, at two or more Z-axis positions, of an area of the circuit board which includes the electrical connection; and comparing and analyzing the two or more cross sectional images at the two or more Z-axis positions, and deriving therefrom the Z-axis position of the electrical connection. This method may further include the step of determining a reference Z-axis position, $Z_{RF}$. In some configurations, the method further comprises the steps of: acquiring a first cross sectional image of the electrical connection at a first Z-axis position, $Z_{RF}+\Delta Z_1$, and a second cross sectional image of the electrical connection at a second Z-axis position, $Z_{RF}+\Delta Z_2$; determining a first plurality of gradients for the first cross sectional image and a second plurality of gradients for the second cross sectional image; calculating a first variance for the first plurality of gradients corresponding to the first cross sectional image at the first Z-axis position, $Z_{RF}+\Delta Z_1$, and a second variance for the second plurality of gradients corresponding to the second cross sectional image at the second Z-axis position, $Z_{RF}+\Delta Z_2$; and analyzing the first and second variances and deriving therefrom the Z-axis position of the electrical connection. In this method, the image gradients may be approximated over a K×K pixel grid by the following relation:

$$G_{MR}[f(x,y)] \approx |f(x-N,y-N)-f(x+M,y+M)|+|f(x+M,y-N)-f(x-N,y+M)|$$

where $f(x,y)$ represents a gray value of a pixel located at x,y; K is an integer which is greater than or equal to 2; N=(K−1)/2 rounded down to the nearest integer; and M=K−N−1. In some configurations, the reference Z-axis position is determined with a range finder which may include a laser range finder. The method may further include the steps of: determining a Z-axis position for substantially all of the electrical connections on the circuit board; storing the Z-axis positions for substantially all of the electrical connections on the circuit board in a data base; selecting a first board view which includes a first portion of the circuit board; and deriving from the stored values of the Z-axis positions for the electrical connections included within the first board view, a Z-axis position for the first board view.

In a seventh aspect, the invention is a device for inspecting electrical connections on a circuit board comprising: means for acquiring two or more cross sectional images, at two or more Z-axis positions, of an area of the circuit board which includes the electrical connection; and means for comparing and analyzing the two or more cross sectional images at the two or more Z-axis positions, and deriving therefrom the Z-axis position of the electrical connection. In some configurations, the device further comprises: means for determining a reference Z-axis position, $Z_{RF}$; means for acquiring a first cross sectional image of the electrical connection at a first Z-axis position, $Z_{RF}+\Delta Z_1$, a second cross sectional image of the electrical connection at a second Z-axis position, $Z_{RF}+\Delta Z_2$, and a third cross sectional image of the electrical connection at a third Z-axis position, $Z_{RF}+\Delta Z_3$; means for determining a first plurality of gradients for the first cross sectional image, a second plurality of gradients for the second cross sectional image and a third plurality of gradients for the third cross sectional image; means for calculating a first variance for the first plurality of gradients corresponding to the first cross sectional image at the first Z-axis position, $Z_{RF}+\Delta Z_1$, a second variance for the second plurality of gradients corresponding to the second cross sectional image at the second Z-axis position, $Z_{RF}+\Delta Z_2$, and third variance for the third plurality of gradients corresponding to the third cross sectional image at the third Z-axis position, $Z_{RF}+\Delta Z_3$; and means for determining a maximum variance value derived from the first, second and third variances and selecting a corresponding Z-axis position, $Z_{RF}+\Delta Z_{MAX}$, corresponding to the maximum variance value, as the Z-axis position of the electrical connection. In some configurations, this device may further comprise a surface mapper for creating a surface map of the circuit board.

These and other characteristics of the present invention will become apparent through reference to the following detailed description of the preferred embodiments and accompanying drawings.

BRIEF DESCRIPTION OF THE INVENTION

FIG. 2e shows a conventional, two-dimensional X-ray projection image of the object in FIG. 2a.

FIG. 3a is a diagrammatic cross-sectional view of a circuit board inspection laminography system showing how the laminographic image is formed and viewed by a camera.

FIG. 3b shows a top view enlargement of an inspection region shown in FIG. 3a.

FIG. 3c is a perspective view of the circuit board inspection laminography system shown in FIG. 3a.

Figure 1:
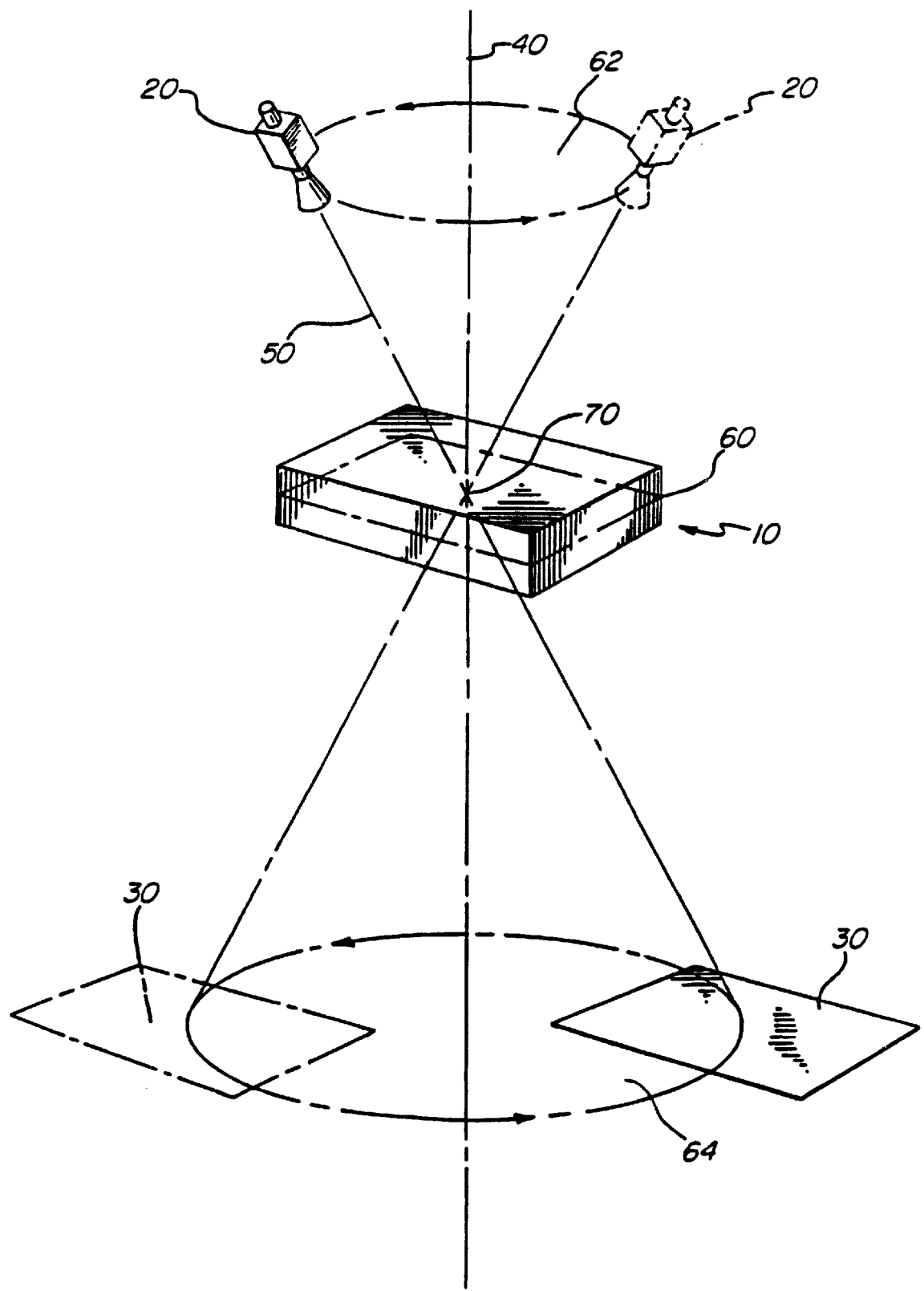
FIG. 1 is a schematic representation of a laminography system illustrating the principles of the technique.

REFERENCE NUMERALS IN DRAWINGS 10 object under inspection
20 source of X-rays
30 X-ray detector
40 common axis of rotation
50 central ray
60 image plane in object 10
60a arrow image plane
60b circle image plane
60c cross image plane
62 plane of source of X-rays
64 plane of X-ray detector
70 point of intersection
81 arrow test pattern
82 circle test pattern
83 cross test pattern
100 image of arrow 81
102 blurred region
110 image of circle 82
112 blurred region
120 image of cross 83
122 blurred region
130 image of arrow 81
132 image of circle 82
134 image of cross 83
200 X-ray tube
210 printed circuit board
212 electronic components
214 electrical connections
220 support fixture
230 positioning table
240 rotating X-ray detector
250 fluorescent screen
252 first mirror
254 second mirror
256 turntable
258 camera
260 feedback system
262 input connection
263 sensor
264 output connection
265 position encoder
270 computer
276 input line
278 output line
280 rotating source spot
281 deflection coils
282 X-rays
283 region of circuit board
284 X-rays
285 rotating electron beam
286 light
287 target anode
290 granite support table
292 load/unload port
294 operator station
296 laser range finder
300 laser surface map points
302 board view center
304 surface map triangles
310 printed circuit board
312 electronic components
314 connections/solder joints
316 Z-axis reference plane
317 Z-axis reference plane
318 triangular mesh
320 solder pads
324 circuit board surfaces
340 cross sectional image planes
400 flowchart
404–432 flowchart activity blocks
500 plot of variances
504 variance data points
508 parabolic curve
512 parabola peak
610 circuit board
612 BGA device
614 solder balls
616 device contact pads
620 circuit board contact pads
640 cross sectional image planes
710 circuit board
712 electronic components
714 electrical connections
730 board views

DETAILED DESCRIPTION OF THE PREFERRED EMBODIMENTS

As used throughout, the term "radiation" refers to electromagnetic radiation, including but not limited to the X-ray, gamma and ultraviolet portions of the electromagnetic radiation spectrum.

CROSS-SECTIONAL IMAGE FORMATION

FIG. 1 shows a schematic representation of a typical laminographic geometry used with the present invention. An object 10 under examination, for example, a circuit board, is held in a stationary position with respect to a source of X-rays 20 and an X-ray detector 30. Synchronous rotation of the X-ray source 20 and detector 30 about a common axis 40 causes an X-ray image of the plane 60 within the object 10 to be formed on the detector 30. The image plane 60 is substantially parallel to the planes 62 and 64 defined by the rotation of the source 20 and detector 30, respectively. The image plane 60 is located at the intersection 70 of a central ray 50 from the X-ray source 20 and the common axis of rotation 40. This point of intersection 70 acts as a fulcrum for the central ray 50, thus causing an in-focus cross-sectional X-ray image of the object 10 at the plane 60 to be formed on detector 30 as the source and detector synchronously rotate about the intersection point 70. Structure within the object 10 which lies outside of plane 60 forms a blurred X-ray image on detector 30.

In the laminographic geometry shown in FIG. 1, the axis of rotation of the radiation source 20 and the axis of rotation of the detector 30 are coaxial. However, it is not necessary that these axes of rotation of the radiation source 20 and the detector 30 be coaxial. The conditions of laminography are satisfied and a cross-sectional image of the layer 60 will be produced as long as the planes of rotation 62 and 64 are mutually parallel, and the axes of rotation of the source and the detector are mutually parallel and fixed in relationship to each other. Coaxial alignment reduces the number of constraints upon the mechanical alignment of the apparatus.

FIGS. 2a–2e show laminographs produced by the above described laminographic technique. The object 10 shown in FIG. 2a has test patterns in the shape of an arrow 81, a circle 82 and cross 83 embedded within the object 10 in three different planes 60a, 60b and 60c, respectively.

Figure 2A:
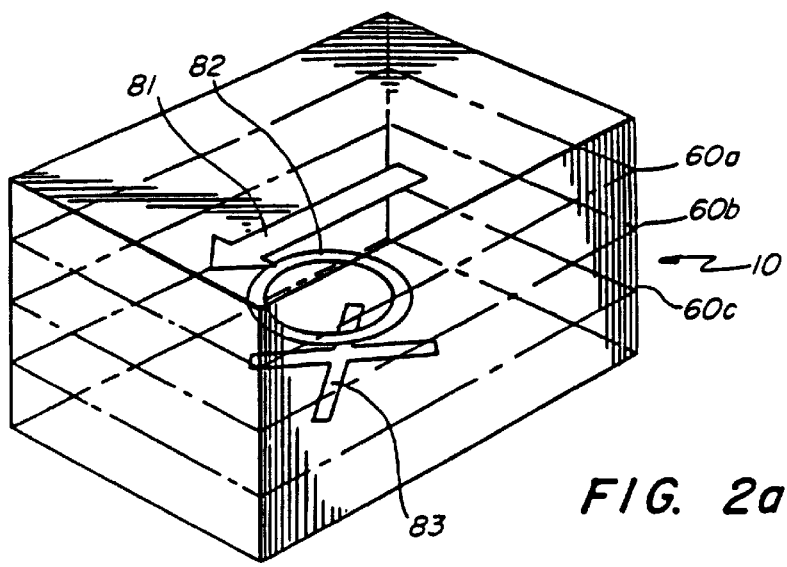
FIG. 2a shows an object having an arrow, a circle and a cross embedded in the object at three different planar locations.
Figure 2B:
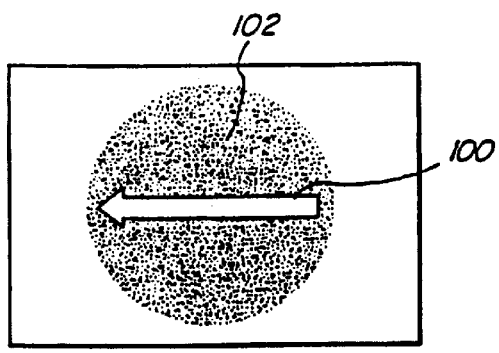
FIG. 2b shows a laminograph of the object in FIG. 2a focused on the plane containing the arrow.

FIG. 2b shows a typical laminograph of object 10 formed on detector when the point of intersection 70 lies in plane 60a of FIG. 2a. The image 100 of arrow 81 is in sharp focus, while the images of other features within the object 10, such as the circle 82 and cross 83 form a blurred region 102 which does not greatly obscure the arrow image 100.

Figure 2D:
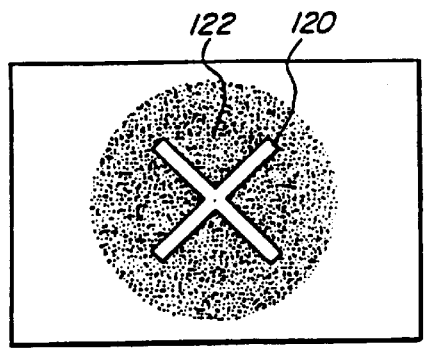
FIG. 2d shows a laminograph of the object in FIG. 2a focused on the plane containing the cross.
Figure 2C:
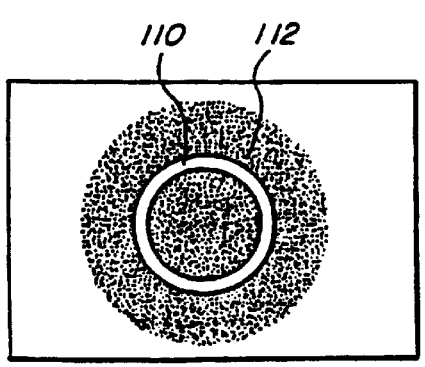
FIG. 2c shows a laminograph of the object in FIG. 2a focused on the plane containing the circle.

Similarly, when the point of intersection 70 lies in plane 60b, the image 110 of the circle 82 is in sharp focus as seen in FIG. 2c. The arrow 81 and cross 83 form a blurred region 112.

FIG. 2d shows a sharp image 120 formed of the cross 83 when the point of intersection 70 lies in plane 60c. The arrow 81 and circle 82 form blurred region 122.

Figure 2E:
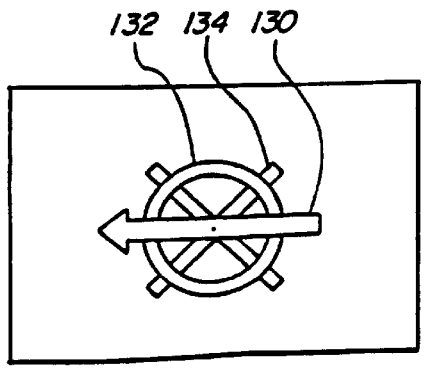

For comparison, FIG. 2e shows an X-ray shadow image of object 10 formed by conventional projection radiography techniques. This technique produces sharp images 130, 132 and 134 of the arrow 81, circle 82 and cross 83, respectively, which overlap one another. FIG. 2e vividly illustrates how multiple characteristics contained within the object 10 may create multiple overshadowing features in the X-ray image which obscure individual features of the image.

FIG. 3a illustrates a schematic diagram of a typical laminographic apparatus used with the present invention. In this configuration, an object under inspection is a printed circuit board 210 having multiple electronic components 212 mounted on the board 210 and electrically interconnected via electrical connections 214 (See FIG. 3b). Typically, the electrical connections 214 are formed of solder. However, various other techniques for making the electrical connections 214 are well know in the art and even though the invention will be described in terms of solder joints, it will be understood that other types of electrical connections 214 including, but not limited to, conductive epoxy, mechanical, tungsten and eutectic bonds may be inspected utilizing the invention. FIG. 3b, which is a top view enlargement of a region 283 of the circuit board 210, more clearly shows the components 212 and solder joints 214.

The laminographic apparatus acquires cross-sectional images of the solder joints 214 using the previously described laminographic method or other methods capable of producing equivalent cross-sectional images. The cross-sectional images of the solder joints 214 are automatically evaluated to determine their quality. Based on the evaluation, a report of the solder joint quality is presented to the user.

The laminographic apparatus, as shown in FIG. 3a, comprises an X-ray tube 200 which is positioned adjacent printed circuit board 210. The circuit board 210 is supported by a fixture 220. The fixture 220 is attached to a positioning table 230 which is capable of moving the fixture 220 and board 210 along three mutually perpendicular axes, X, Y and Z. A rotating X-ray detector 240 comprising a fluorescent screen 250, a first mirror 252, a second mirror 254 and a turntable 256 is positioned adjacent the circuit board 210 on the side opposite the X-ray tube 200. A camera 258 is positioned opposite mirror 252 for viewing images reflected into the mirrors 252, 254 from fluorescent screen 250. A feedback system 260 has an input connection 262 from a sensor 263 which detects the angular position of the turntable 256 and an output connection 264 to X and Y deflection coils 281 on X-ray tube 200. A position encoder 265 is attached to turntable 256. The position sensor 263 is mounted adjacent encoder 265 in a fixed position relative to the axis of rotation 40. The camera 258 is connected to a computer 270 via an input line 276. The computer 270 includes the capability to perform high speed image analysis. An output line 278 from the computer 270 connects the computer to positioning table 230. A laser range finder 296 is positioned adjacent the circuit board 210 for creating a Z-map of the surface of the circuit board 210.

Figure 3C:
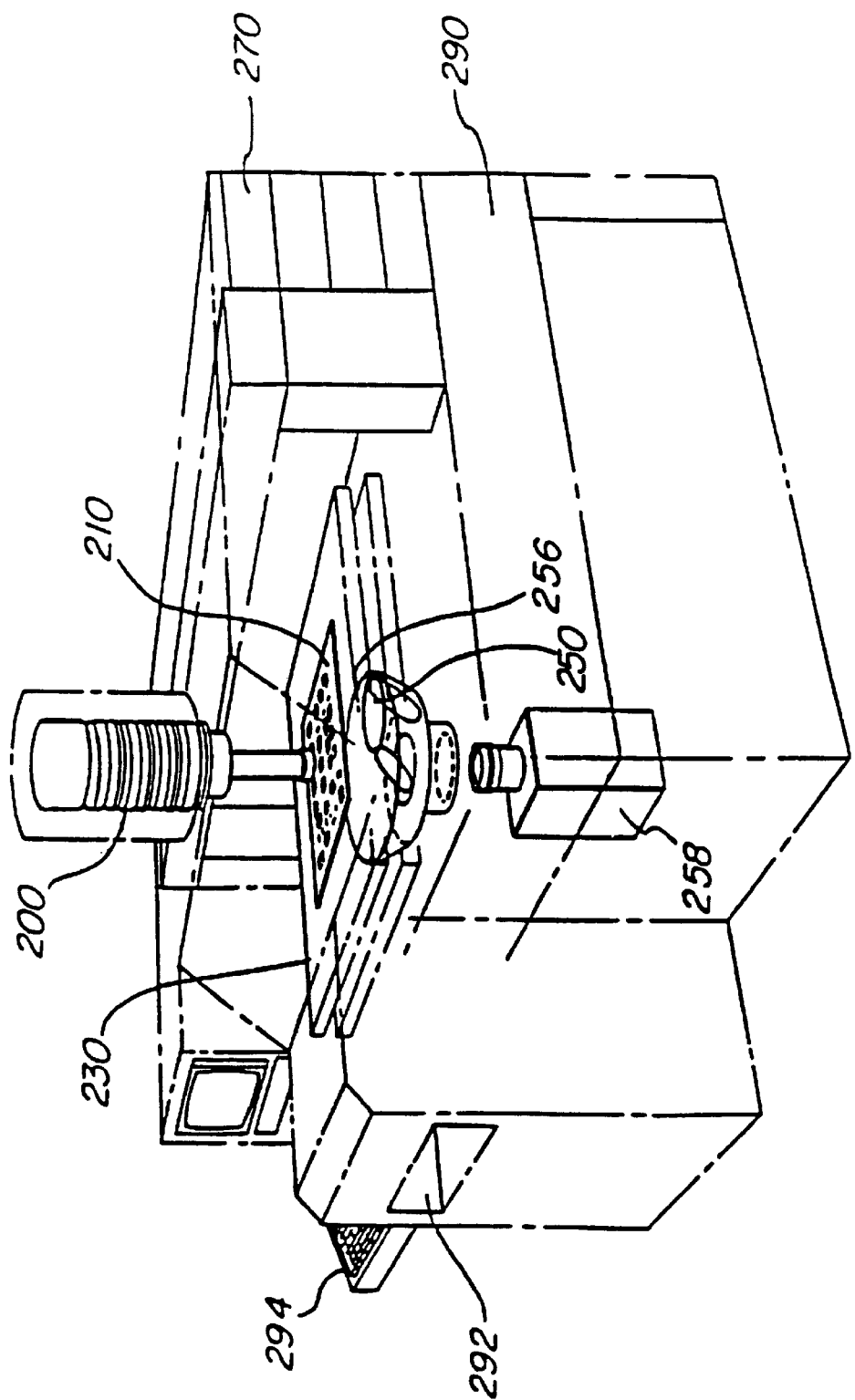

A perspective view of the laminographic apparatus is shown in FIG. 3c. In addition to the X-ray tube 200, circuit board 210, fluorescent screen 250, turntable 256, camera 258, positioning table 230 and computer 270 shown in FIG. 3a, a granite support table 290, a load/unload port 292 and an operator station 294 are shown. The granite table 290 provides a rigid, vibration free platform for structurally integrating the major functional elements of the laminographic apparatus, including but not limited to the X-ray tube 200, positioning table 230 and turntable 256. The load/unload port 292 provides a means for inserting and removing circuit boards 210 from the machine. The operator station 294 provides an input/output capability for controlling the functions of the laminographic apparatus as well as for communication of inspection data to an operator.

In operation of the laminographic apparatus as shown in FIGS. 3a and 3c, high resolution, cross-sectional X-ray images of the solder joints 214 connecting components 212 on circuit board 210 are acquired using the X-ray laminographic method previously described in reference to FIGS. 1 and 2. Specifically, X-ray tube 200, as shown in FIG. 3a, comprises a rotating electron beam spot 285 which produces a rotating source 280 of X-rays 282. The X-ray beam 282 illuminates a region 283 of circuit board 210 including the solder joints 214 located within region 283. X-rays 284 which penetrate the solder joints 214, components 212 and board 210 are intercepted by the rotating fluorescent screen 250.

Dynamic alignment of the position of the X-ray source 280 with the position of rotating X-ray detector 240 is precisely controlled by feedback system 260. The feedback system correlates the position of the rotating turntable 256 with calibrated X and Y deflection values stored in a look-up table (LUT). Drive signals proportional to the calibrated X and Y deflection values are transmitted to the steering coils 281 on the X-ray tube 200. In response to these drive signals, steering coils 281 deflect electron beam 285 to locations on an annular shaped target anode 287 such that the position of the X-ray source spot 280 rotates in synchronization with the rotation of detector 240 in the manner previously discussed in connection with FIG. 1.

X-rays 284 which penetrate the board 210 and strike fluorescent screen 250 are converted to visible light 286, thus creating a visible image of a single plane within the region 283 of the circuit board 210. The visible light 286 is reflected by mirrors 252 and 254 into camera 258. Camera 258 typically comprises a low light level closed circuit TV (CCTV) camera which transmits electronic video signals corresponding to the X-ray and visible images to the computer 270 via line 276. The image analysis feature of computer 270 analyzes and interprets the image to determine the quality of the solder joints 214.

Computer 270 also controls the movement of positioning table 230 and thus circuit board 210 so that different regions of circuit board 210 may be automatically positioned within inspection region 283.

The laminographic geometry and apparatus shown and described with reference to FIGS. 1–3 are typical of that which may be used in conjunction with the present invention. However, specific details of these systems are not critical to the practice of the present invention, which addresses the accurate positioning of the circuit board 210 along the Z-axis 40 of the system. For example, the number of computers and delegation of tasks to specific computers may vary considerably from system to system as may the specific details of the X-ray source, detector, circuit board positioning mechanism, etc. One skilled in the art will also recognize that other techniques, for example computed tomography, may be used to produce cross sectional images of specific planes within a solder joint. Furthermore, specific details of various techniques and equipment for creating a Z-map of the surface of the circuit board may be utilized. The present invention is applicable to any type of system which generates cross sectional images of specific planes within a test object and requires accurate determination of Z-axis location within the test object.

LASER SURFACE MAPPING

Figure 4A:
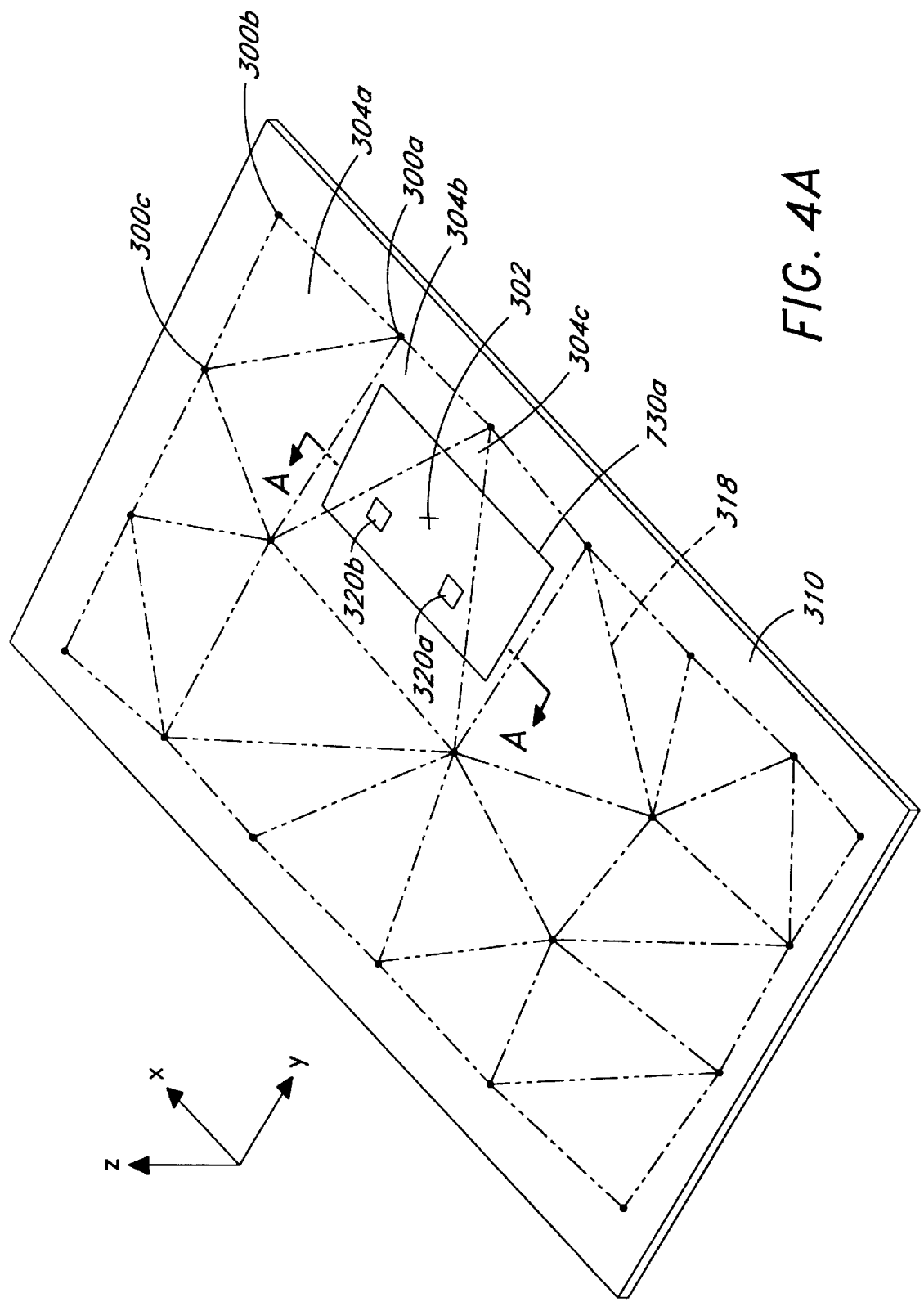
FIGS. 4a, 4b and 4c illustrate triangular mesh laser surface maps of circuit boards.
Figure 4B:
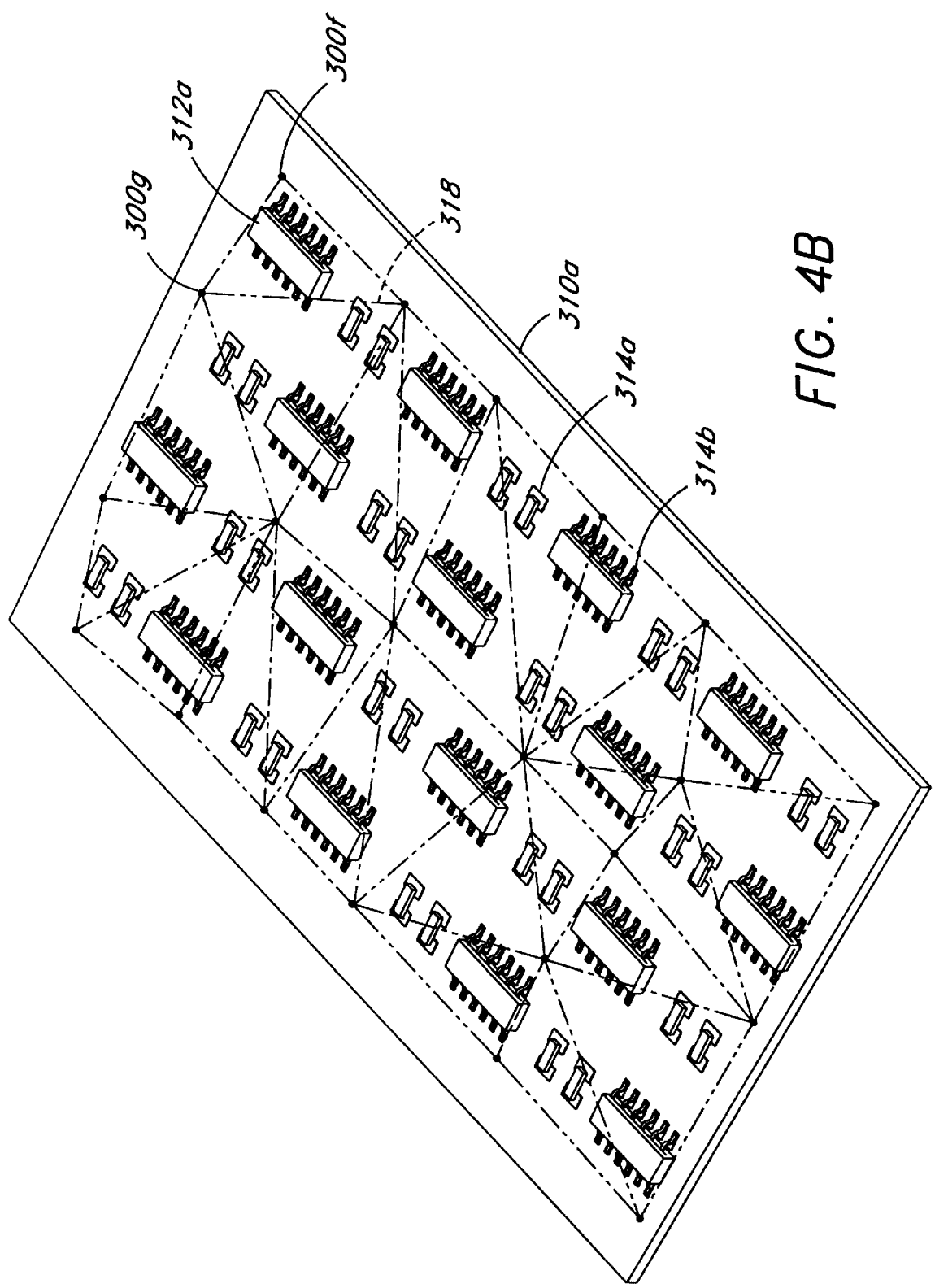
Figure 4C:
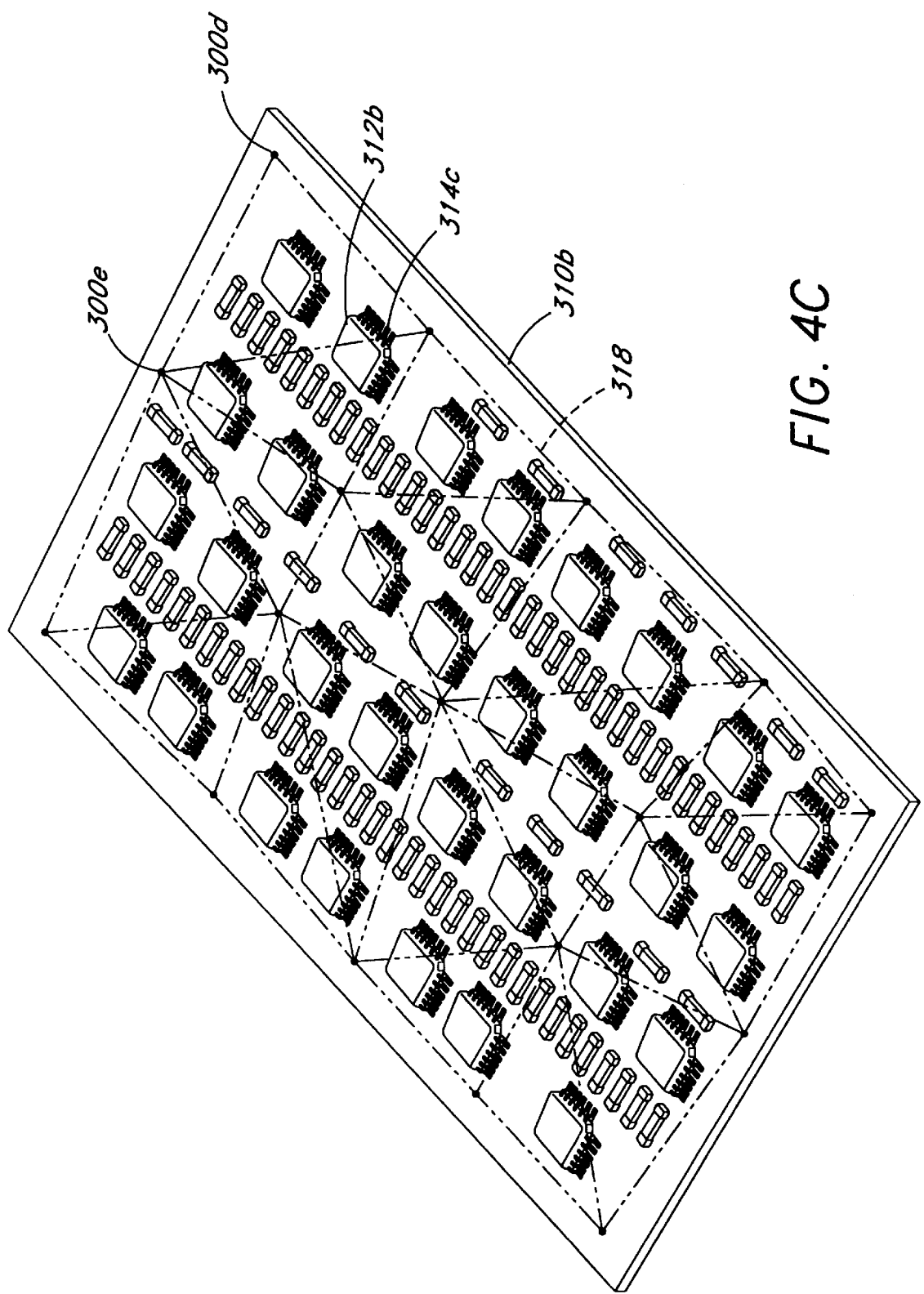

Shown in FIGS. 4a, 4b and 4c are printed circuit boards 310 with a plurality of laser surface map points 300 used to create Z-maps of the surface of the circuit boards 310. Referring to FIG. 4a, the laser surface map points 300a, 300b, 300c, etc. are interconnected to form a series of individual surface map triangles 304a, 304b, etc. which together form a triangular mesh 318 which represents a "backbone" for the board 310. For clarity of illustrating the surface map triangles 304 and the triangular mesh 318, the circuit board 310 shown in FIG. 4a shows only 2 solder pads 320a and 320b located within a board view 730a. Board view 730a has a center location 302. Other electrical components which would typically be mounted to the board 310 are not shown. FIGS. 4b and 4c illustrate laser map triangular meshes 318 superimposed on circuit boards 310a and 310b which have a variety of electronic components 312 attached to the circuit board 310 by solder connections 314.

In operation, the laser range finder 296 determines a Z-axis distance for each of the laser surface map points 300 on the surface of the board 310. The locations of the laser surface map points 300 on the surface of the circuit board 310 are predetermined by the specific design and layout of components 312 on the board 310 and the inspection criteria for specific regions of the board 310. It is preferred that the laser map points 300 be located near the solder joints 314 being inspected. Additionally, the size of the each triangle 304 forming the mesh is determined by the availability of laser map points 300 which do not interfere with components 312 mounted to board 310 and the desired accuracy of the Z-map for specific regions of the board 310. For example, specific regions of the board 310 may have characteristics which require a smaller triangle 304 to accurately reflect the Z elevation of the solder joints 314 located within that region 304.

Figure 5:
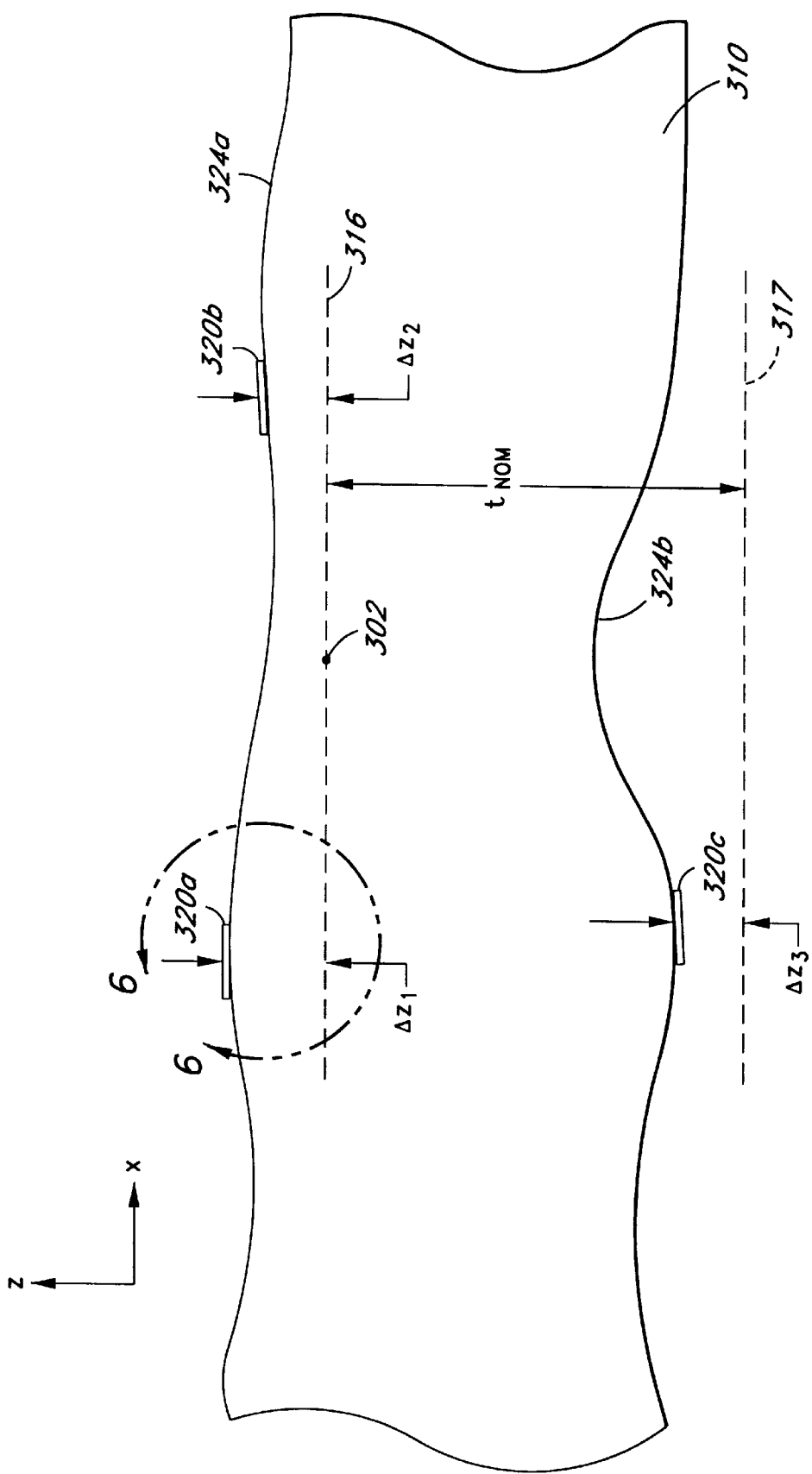
FIG. 5 shows an enlarged cross sectional view of section A—A of the circuit board 310 shown in FIG. 4a and illustrates how the Delta Z values are defined with respect to the solder pads and a Z-axis reference plane.

Typically, this Z-map of the surface of the circuit board 310, represented by the triangular mesh 318, does not coincide with the surface of the circuit board 310. In fact, a common problem is that the triangular interpolation is not very accurate and does not match the board surface. This is illustrated in FIG. 5, which shows an enlarged cross sectional view of section A—A of the circuit board 310 shown in FIG. 4a. A Z-axis reference plane 316 corresponding to the board view center 302 of board view 730a is also shown. In this example, the Z-axis reference plane 316 for board view center 302 is determined by reference to surface map triangle 304c (FIG. 4a). One option selects a Z-axis elevation for Z-axis reference plane 316 which corresponds to the Z-axis elevation of the surface map triangle 304c at the XY coordinates which define the board view center 302. In this example, the Z-axis reference plane 316 for board view 730a is a plane which is parallel to the XY plane and is constant for each location of board view 730a. Also shown in FIG. 5 are solder pads 320 on both surfaces 324a and 324b of the circuit board 310. As seen in this exaggerated view, the surfaces 324a and 324b of the circuit board 310 may not be flat and may not even be parallel to the Z-axis reference plane 316. The present invention addresses this problem by automatically measuring and storing the distance, referred to as "Delta Z", between each solder pad 320 and the Z-axis reference plane 316. For example, in FIG. 5, $\Delta Z_1$ and $\Delta Z_2$ represent the Delta Z values for solder pads 320a and 320b located on surface 324a of the circuit board 310. For solder pads on the opposite side of the board from the laser measured surface, Delta Z values are determined by storing the distance between the solder pad and another Z-axis reference plane 317 calculated by adding a nominal board thickness, $t_{NOM}$, to the top reference plane 316. Also, the sign of the Delta Z value opposite the laser measured surface side is inverted to maintain a consistent sign convention. Thus, positive Delta Z values imply the pad lies outside of the two defined reference planes, while negative Delta Z values imply the pad lies within the reference planes. So similarly, $\Delta Z_3$, represents the Delta Z value for solder pad 320c located on surface 324b of the circuit board 310. In the above examples, $\Delta Z_1$, and $\Delta Z_2$ have positive values because the pads lie outside the reference surfaces, while $\Delta Z_3$ has a negative value because the pad lies inside the reference surfaces. While not shown, it should be noted that in cases of extreme board warpage, the Delta Z values for a solder pad located on surface 324a may have both positive and negative values. In other words, the Z-axis reference plane 316 may be located above the board surface 324a in some areas and below the board surface 324a in other areas. There are numerous other options for selecting Z-axis reference elevations for a board view or for individual locations within a board view. Several alternatives for determining a Z-axis reference(s) for a board view with respect to the triangular mesh 318 include: 1) the average Z-axis elevation of the surface map triangle 304 within which a major portion of a board view 730 is located; 2) an interpolated Z-axis elevation of the surface map triangle 304 corresponding to the XY coordinates which define the center (or other selected location) of a board view 730; 3) a plurality of interpolated Z-axis elevations of the surface map triangle 304 corresponding to the XY coordinates which define specific solder pads 320 located within of a board view 730; etc.

Alternatively, a Z-map of the surface of the circuit board may be created by measuring the Z-axis coordinates of a selected subset of the solder joints/solder pads on the circuit board using X-ray images. In this manner, the laser range finder is eliminated and the laser surface map points are replaced by "solder joint/solder pad surface map points".

DETERMINATION OF DELTA Z (ΔZ) VALUES

Figure 6:
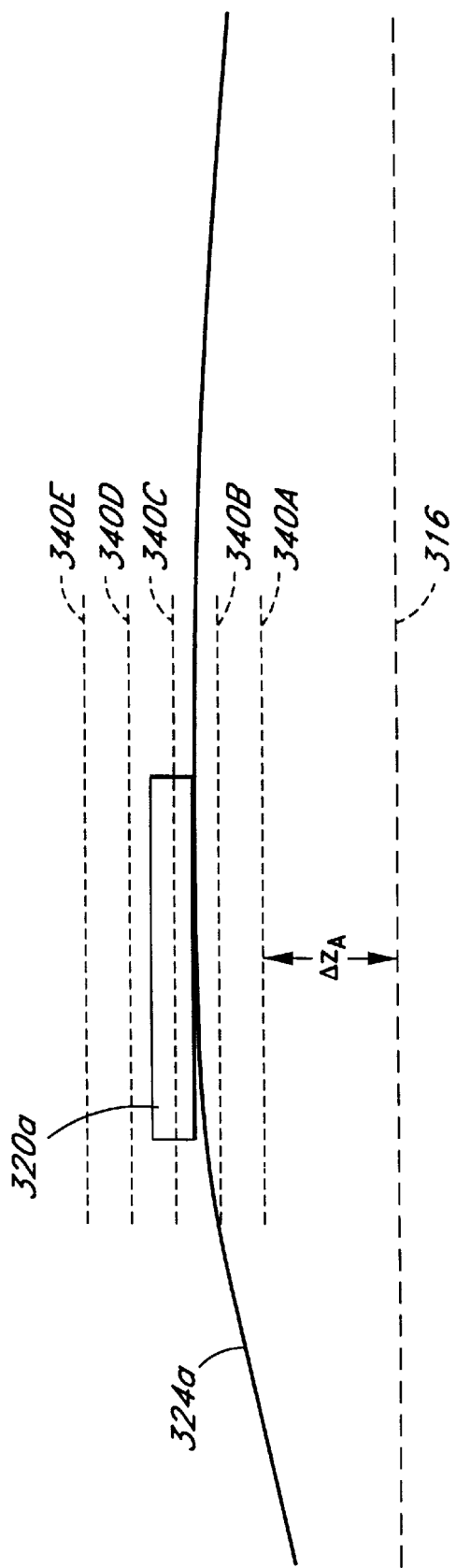
FIG. 6 shows an enlargement of the solder pad 320a in FIG. 5.

A Delta Z value for each solder pad 320 on the circuit board 310 is determined in the following manner. Referring to FIG. 6, which shows an enlargement of the solder pad 320a in FIG. 5, a series of laminographic cross sectional images of the solder pad 320a are acquired. For example, as shown in FIG. 6, five cross sectional images, corresponding to image planes 340A, 340B, 340C, 340D and 340E, are obtained at five different ΔZ values which bracket the Z-axis location of solder pad 320a. In this example, the Delta Z value for image plane 340A is the distance between the image plane 340A and the Z-axis reference plane 316 and is designated as $\Delta Z_A$. Similarly, the distances between the image planes 340B, 340C, 340D and 340E and the Z-axis reference plane 316 are designated as $\Delta Z_B$, $\Delta Z_C$, $\Delta Z_D$ and $\Delta Z_E$, respectively. The image plane which most accurately reflects the distance between the solder pad 320a and the Z-axis reference plane 316 is image plane 340C. Thus, for the example shown in FIG. 6, the Delta Z for solder pad 320a is $\Delta Z_C$.

The apparatus and method of the present invention determines that $\Delta Z_C$ is the most accurate value of Delta Z for solder pad 320a by analyzing the five cross sectional images of the solder pad 320a obtained at image planes 340A, 340B, 340C, 340D and 340E. Generally, the image which exhibits the best focus is formed at the image plane which most accurately corresponds to the location of the solder pad 320a. The image exhibiting the best focus of the solder pad 320a may be determined by a number of different focus quality parameters. For example, the image which displays the sharpest edges, i.e., the highest variance of the gradients of the image, may be selected as the image exhibiting the best focus. In the example shown in FIG. 6, when the variance of the gradients of the five images formed at the image planes 340A, 340B, 340C, 340D and 340E are computed and compared, the cross sectional image of the solder pad 320a formed at image plane 340C exhibits the highest variance of the gradient. While the example shown in FIG. 6 shows five image planes, it is to be understood that a different number of image planes, either less than or greater than five, may be selected in practicing the present invention. Additionally, interpolation between the focus quality parameter, e.g., sharpness, of the images corresponding to the image planes 340A, 340B, 340C, 340D and 340E may be used to determine an interpolated Delta Z for the solder pad 320a.

Figure 7A:
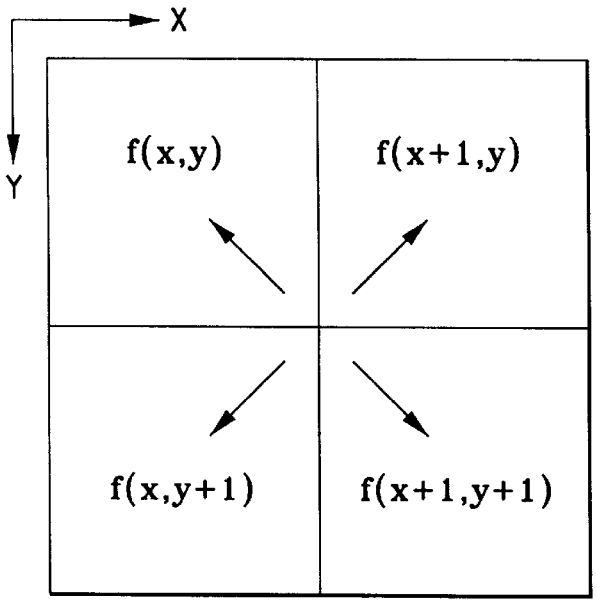
FIG. 7a illustrates the procedure for computing the two-dimensional, discrete Robert's gradient of an image.
Figure 7B:
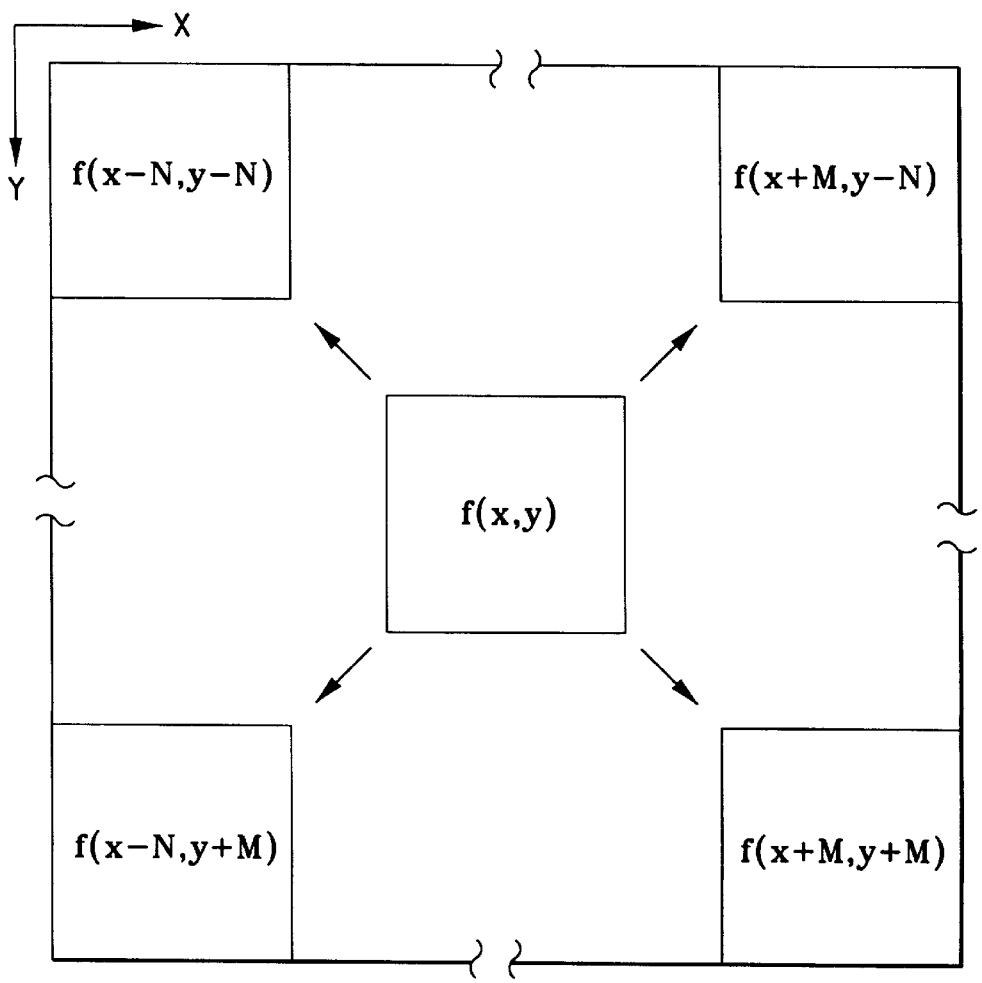
FIG. 7b illustrates the procedure for computing the two-dimensional, discrete modified Robert's gradient of an image.

One standard way to approximate the gradient of an image is known as Robert's gradient which is given by the following relation:

$$G_R[f(x,y)] \approx |f(x,y)-f(x+1,y+1)|+|f(x+1,y)-f(x,y+1)|$$

where f(x,y) represents the gray value of the pixel located at x,y in an I X J pixel size image. The procedure for determining Robert's gradient, $G_R$, is illustrated is FIG. 7a. A generalization of this procedure is actually preferred for the present invention. Instead of approximating the gradient over a 2×2 pixel grid, a modified Robert's gradient ($G_{MR}$) is approximated over an adjustable kernal size K which is greater than or equal to 2. The modified Robert's gradient ($G_{MR}$) is approximated in a K×K pixel grid by the following relation:

$$G_{MR}[f(x,y)] \approx |f(x-N,y-N)-f(x+M,y+M)|+|f(x+M,y-N)-f(x-N,y+M)|$$

where K is an integer which is greater than or equal to 2; N=(K−1)/2 rounded down to the nearest integer; and M=K−N−1. For example, for K=2, N=0 and M=1, for K=3, N=1 and M=1, for K=4, N=1 and M=2, for K=5, N=2 and M=2, etc. This procedure for determining the modified Robert's gradient, $G_{MR}$, is illustrated in FIG. 7b. The edge frequency may be tuned by adjusting the kernal size K. Robert's gradient and other techniques for analyzing digital images are described in a book authored by Rafael C. Gonzalez and Paul Wintz entitled "Digital Image Processing", Addison Wesley Publishing Company, Inc., 1987, the entire contents of which are hereby incorporated herein by reference.

After determining the gradient for multiple pixels comprising the image for each of the cross sectional images of the solder pad 320a obtained at image planes 340A, 340B, 340C, 340D and 340E, the variance of the gradients for each image, $V_A(G)$, $V_B(G)$, $V_C(G)$, $V_D(G)$ and $V_E(G)$ is calculated using standard techniques for calculating variances. The variances are then compared to determine which image has the largest/maximum value of the variance of the gradients, V(G). In the example shown in FIG. 6, the variance of the gradients $V_C(G)$ for the cross sectional image of the solder pad 320a obtained at image plane 340C is the maximum. Thus, since $\Delta Z_C$ is the Delta Z value at which image plane 340C is located, $\Delta Z_C$ is assigned as the Delta Z value for solder pad 320a. In this idealized example, the variance of the gradients $V_C(G)$ is the maximum and is symmetrical with its neighboring image planes 340B and 340D. However, it is more likely that this will not be the case. Therefore, interpolation between the variances of the gradients $V_A(G)$, $V_B(G)$, $V_C(G)$, $V_D(G)$ and $V_E(G)$, for neighboring image planes may be used to determine the largest/maximum value of the variance of the gradients, V(G). Delta Z for the solder pad 320a is then set equal to an interpolated ΔZ corresponding to the interpolated largest/maximum value of the variance of the gradients, V(G).

Figure 8:
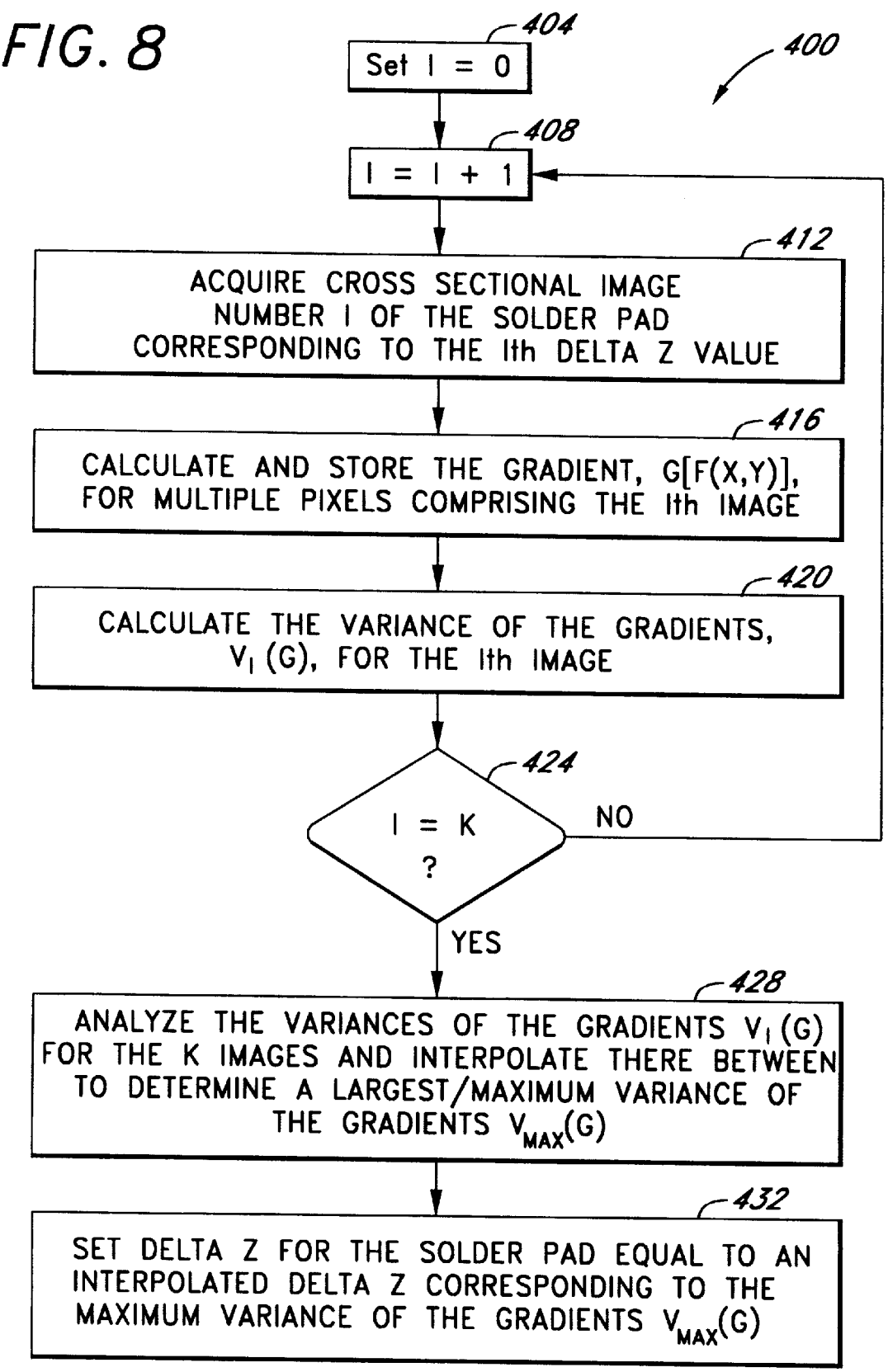
FIG. 8 shows a flowchart which summarizes the procedure for automatically determining a Delta Z value for each solder pad on a circuit board.

A generalized outline of the above procedure for determining a Delta Z value for each solder pad 320 on the circuit board 310 is shown in the flowchart 400 of FIG. 8. Activity blocks 404, 408, 412, 416, 420 and 424 form an iterative loop for: A) acquiring a plurality K of cross sectional images of the solder pad 320 at a plurality K of Delta Z values where each of the Delta Z values for the image planes, i.e., the distances between the image planes and the Z-axis reference plane 316, has a different value (activity block 412); B)

calculating and storing the Gradient, G[f(x,y)], for multiple pixels comprising each of the K images (activity block 416); and C) calculating the Variance of the Gradients, $V_f(G)$, for each of the K images (activity block 420). Preferably, the range of Delta Z values is selected to bracket the design and/or empirically determined approximate Delta Z value, i.e., Z-axis location, of the solder pad 320. In activity block 428, the Variances of the Gradients, $V_f(G)$, for the K images are analyzed and interpolation is used to determine a largest/maximum value, $V_{Max}(G)$, of the Variances of the Gradients, $V_f(G)$. In activity block 432, Delta Z for solder pad 320 is set equal to the interpolated value of Delta Z corresponding to the largest/maximum value, $V_{Max}(G)$, of the Variances of the Gradients, $V_f(G)$.

While the above description determines, via cross sectional images of the solder pad 320a, the actual Z-axis location of the solder pad 320a by analyzing the focus, i.e., sharpness, of the images, one skilled in the art will recognize that alternative methods may be used to determine, also via cross sectional images of a solder pad 320/solder joint 314, the actual Z-axis location of the solder pad 320/solder joint 314. Numerous other parameters including other image quality parameters, geometrical parameters, etc. may be used to determine the actual Z-axis locations of the solder pad 320/solder joint 314. Furthermore, it may be advantageous to perform additional image processing techniques on the images, including but not limited to smoothing, blurring, etc., during the analysis of the images. These image processing and analysis methods are to be understood as being included within the scope of the present invention.

In the example shown in FIG. 6, image plane 340C is shown as intercepting the midpoint of the solder pad 320a and will thus exhibit the maximum value of the variance of the gradients of the multiple images formed at image planes 340A, 340B, 340C, 340D and 340E. However, in practice, it is unlikely that such an idealized situation will prevail. One alternative is that one or more of the image planes may intercept the solder pad, however, not at the midpoint of the solder pad, while the remaining image planes may fall above and below the solder pad. Another alternative is that none of the image planes may intercept the solder pad but may be distributed above and below the solder pad. Yet another alternative is that all of the image planes may be distributed above the solder pad or all of the image planes may be distributed below the solder pad. Thus, it is often advantageous to analyze and/or interpolate the variances of the gradients of the multiple images to determine the best value of ΔZ for a particular family of cross sectional images.

Figure 9:
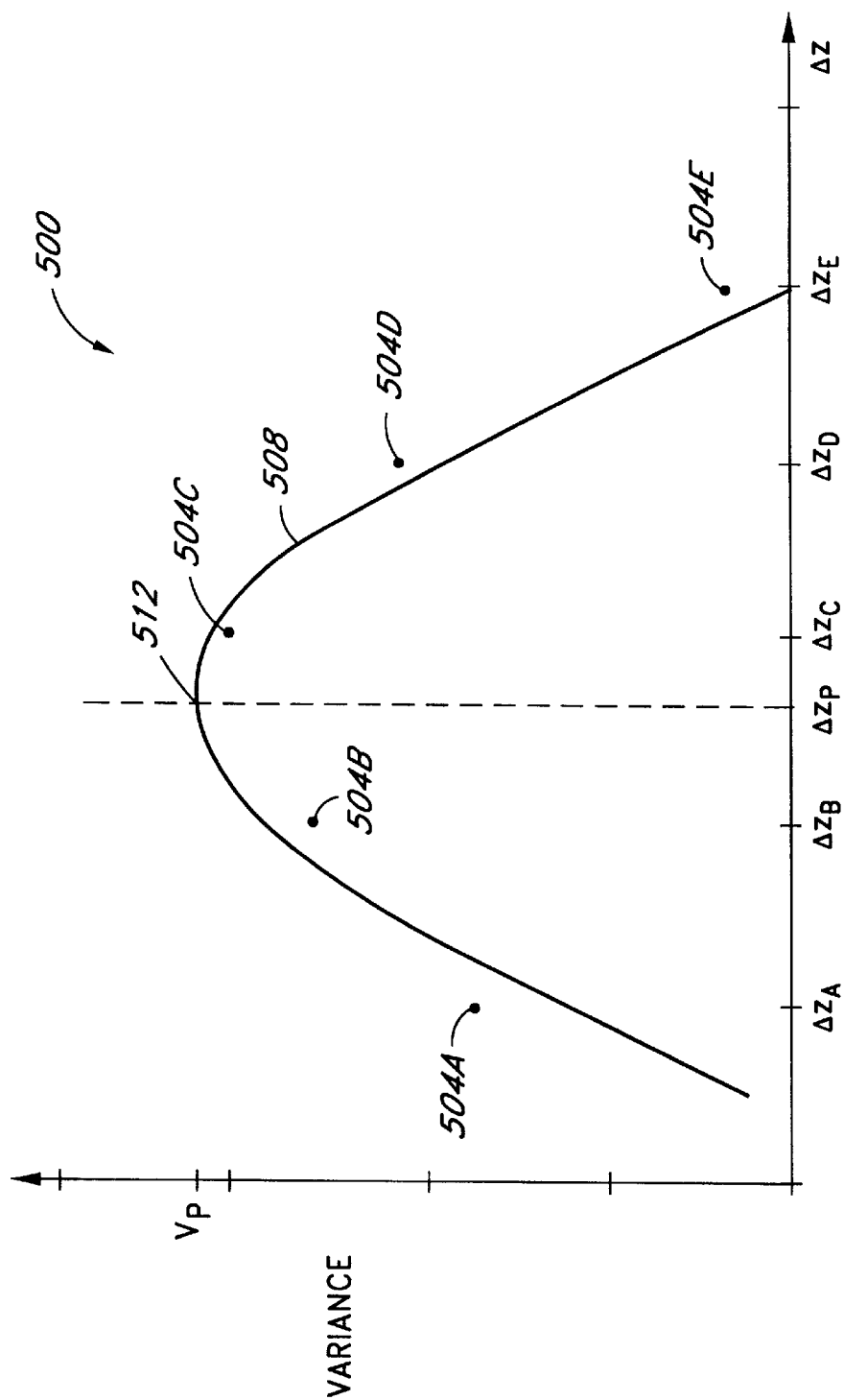
FIG. 9 shows a plot 500 of the variances of the gradients, 504A, 504B, 504C, 504D and 504E, of multiple cross sectional images as a function of the Z-axis locations, $\Delta Z_A$, $\Delta Z_B$, $\Delta Z_C$, $\Delta Z_D$ and $\Delta Z_E$, of the image plane corresponding to each image.

One such analysis technique is illustrated in FIG. 9, which shows a plot 500 of the variances of the gradients, 504A, 504B, 504C, 504D and 504E, of multiple cross sectional images as a function of the Z-axis locations, $\Delta Z_A$, $\Delta Z_B$, $\Delta Z_C$, $\Delta Z_D$ and $\Delta Z_E$, of the image plane corresponding to each image. In this example, a parabolic curve 508 is fit to three or more of the variances of the gradients, 504A, 504B, 504C, 504D and 504E. The ΔZ coordinate corresponding to the peak 512 of the parabolic curve 508, $\Delta Z_P$, is selected as the best value of ΔZ for the family of cross sectional images corresponding to the variances of the gradients, 504A, 504B, 504C, 504D and 504E. Other techniques for determining the best value of ΔZ for a particular family of cross sectional images will be obvious to one of ordinary skill in the art and are to be understood to be included within the scope of the present invention. For example, the variances of the gradients 504A, 504B, 504C, 504D and 504E, may be fit to a different curve other than a parabola, e.g. a hyperbola, a Gaussian, etc.

SPECIAL CASES
BALL GRID ARRAYS (BGA)

Figure 10:
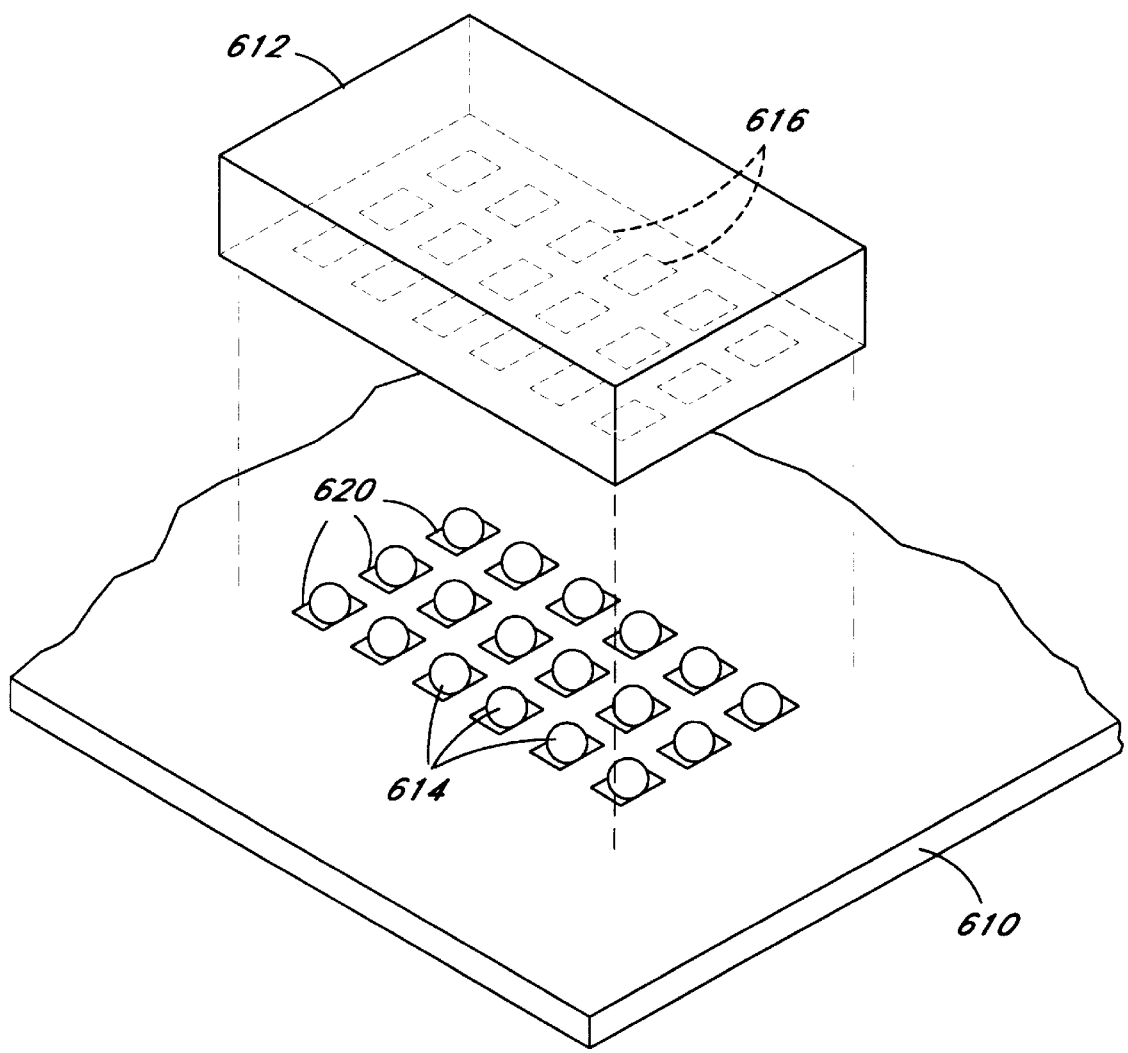
FIG. 10 is a perspective exploded view depicting the manner in which a BGA device is electrically connected to the contact pads on a circuit board forming a Ball Grid Array (BGA).

The above described technique may require modifications as applied to specific types of electronic devices and solder joints. For example, a device, as shown in FIG. 10, commonly referred to as a BGA device, has solder connections which may be analyzed using a modification of the above described technique for determining Delta Z values. In a BGA device, the contact pads are formed in a grid on the underside of the device. A corresponding grid of contact pads is provided on the surface of the circuit board. Balls of solder are formed on the circuit board contact pads. As the contact pad grid on the underside of the BGA device is aligned with the contact pad grid on the surface of the circuit board, and the BGA device is mounted to the circuit board surface, the solder balls provide an electrical connection between the contact pads on the circuit board, and the contact pads on the BGA device. Thus, the solder connections are sandwiched between the bottom surface of the BGA device and the circuit board. These solder connections are referred to as a Ball Grid Array (BGA).

FIG. 10 depicts a BGA device 612 having contact pads 616 on its underside. The BGA device 612 is mounted onto a circuit board 610 having contact pads 620. Also depicted in FIG. 10 are solder balls 614 which provide electrical connections between the contact pads 616 and the contact pads 620 so that a solder joint is formed between each pair of contact pads. Note that most of the solder joints to be inspected are hidden so that they cannot be inspected either visually or by using conventional X-ray inspection. By employing the laminography process described herein however, a cross-sectional view at or near the surface of the circuit board 610 can be taken which allows the solder connections of a BGA device to be analyzed.

Figure 11:
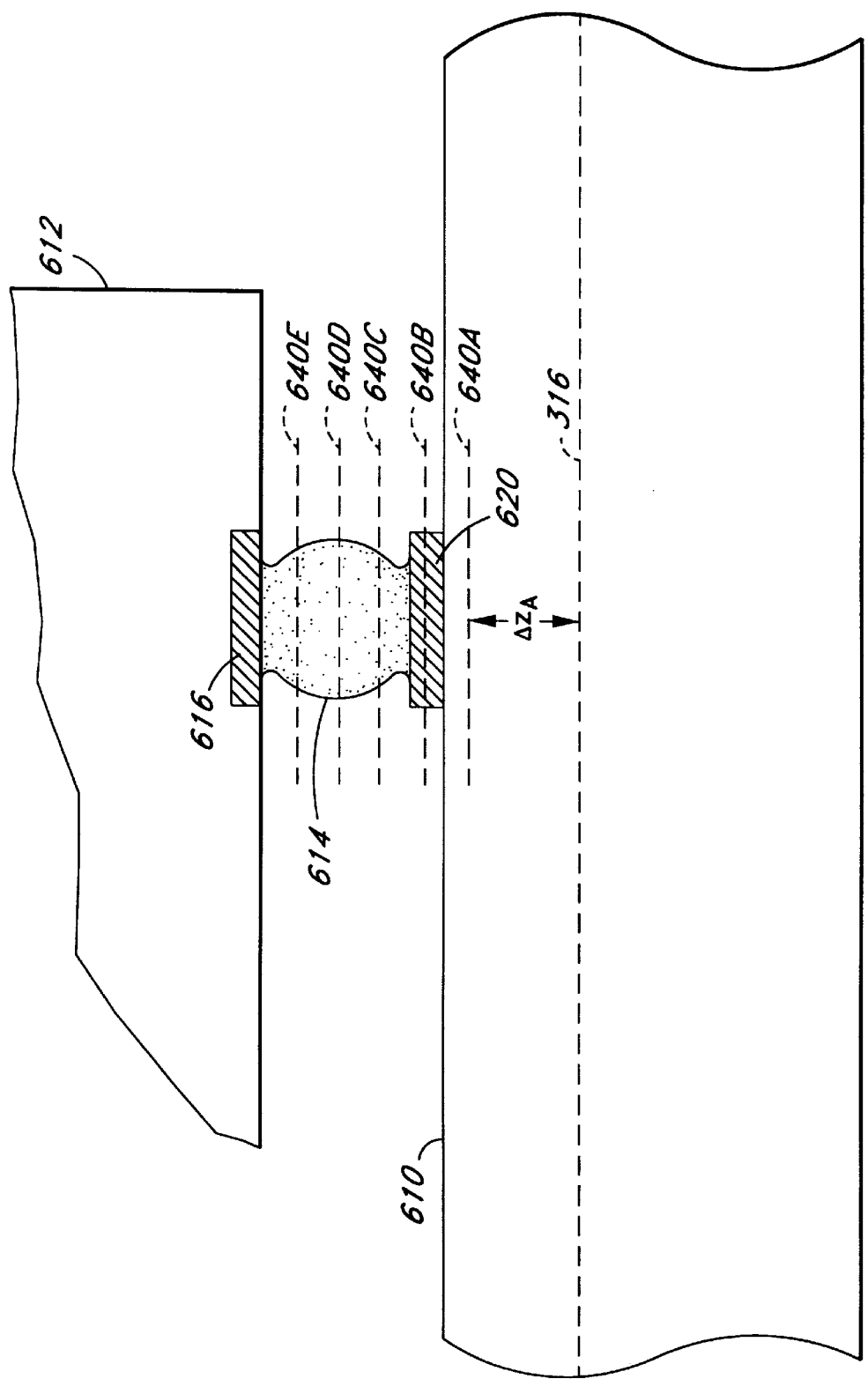
FIG. 11 is an enlarged cross-sectional view showing a side slice of a typical BGA solder connection.

FIG. 11 is an enlarged cross-sectional side view of solder connection 614 between solder pad 616 on BGA device 612 and solder pad 620 on circuit board 610 illustrating typical characteristics of the BGA solder connection 614. As was previously discussed (see FIG. 6), a series of laminographic cross sectional images of the solder pad 620 are acquired. For example, as shown in FIG. 11, five cross sectional images, corresponding to image planes 640A, 640B, 640C, 640D and 640E, are obtained at five different ΔZ values which bracket the Z-axis location of solder connection 614. As before, the Delta Z value for image plane 640A is the distance between the image plane 640A and the Z-axis reference plane 316 and is designated as $\Delta Z_A$. Similarly, the distances between the image planes 640B, 640C, 640D and 640E and the Z-axis reference plane 316 are designated as $\Delta Z_B$, $\Delta Z_C$, $\Delta Z_D$ and $\Delta Z_E$, respectively. The image plane which most accurately reflects the distance between the solder pad 620 and the Z-axis reference plane 316 is image plane 640B. However, analysis of the images formed at image planes 640A, 640B, 640C, 640D and 640E as previously described, i.e., determination of the maximum value of the variances of the gradients of the images formed at image planes 640A, 640B, 640C, 640D and 640E, does NOT yield this result. The result of the previously described analysis is that image plane 640D, which corresponds approximately to the midpoint of the solder connection 614, is the image which exhibits the maximum value of the variances of the gradients of this series of images. This is due to the structure surrounding the BGA solder connection, i.e., the BGA device structure 612 and the circuit board structure 610, in addition to the solder connection 614. However, since the average thickness of the solder connection 614 is generally known, or can be readily determined, the distance from the midpoint of the solder connection 614 to solder pad 620 can be subtracted from the Delta Z value ($\Delta Z_D$) for image plane 640D, to determine the correct Delta Z value for solder pad 620.

As before, the apparatus and method of the present invention determines that $\Delta Z_D$ is the most accurate value of Delta Z for the midpoint of solder connection 614 by analyzing the five cross sectional images obtained at image planes 640A, 640B, 640C, 640D and 640E. The image which has the sharpest edges, i.e., the highest variance of the gradients of the image, is formed at the image plane which most accurately corresponds to the location of the midpoint of solder connection 614. In the example shown in FIG. 11, when the variance of the gradients of the five images formed at the image planes 640A, 640B, 640C, 640D and 640E are computed and compared, the cross sectional image formed at image plane 640D exhibits the highest variance of the gradient. While the example shown in FIG. 11 shows five image planes, it is to be understood that a different number of image planes, either less than or greater than five, may be selected in practicing the present invention.

There is another way to identify the midpoint of solder connection 614 from the images formed at image planes 640A, 640B, 640C, 640D and 640E. This is achieved by analyzing the dimensions of the portion of each image which corresponds to the solder connection 614. The image which exhibits the maximum diameter of the portion corresponding to solder connection 614 identifies the midpoint of the solder connection 614. This technique may be used in addition to or as an alternative to the analysis which determines the midpoint of solder connection 614 by determining which image exhibits the highest variance of the gradients, i.e., is the sharpest. As before, interpolation processes such as those previously discussed with reference to FIG. 9, may be used to determine a Delta Z value, via the midpoint value, which falls between the discrete image planes 640A, 640B, 640C, 640D and 640E.

Circuit Board Inspection

Figure 12:
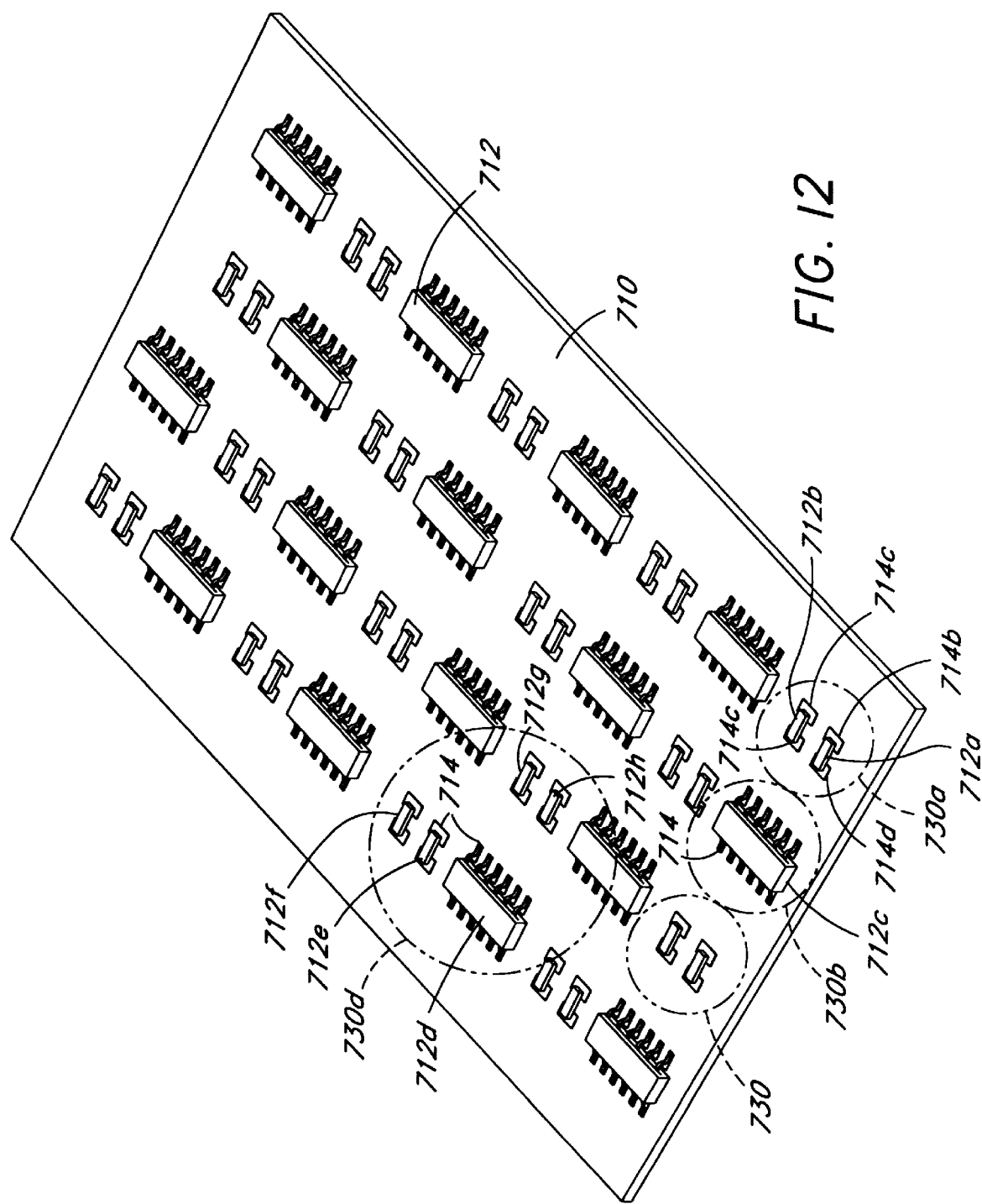
FIG. 12 is a perspective view of the circuit board showing board views used for inspecting solder connections on the circuit board.

The above described techniques are used to inspect circuit boards in the following manner. Typically, the image area, i.e., board view, of laminography systems or other imaging systems which acquire the cross sectional images of connections on the circuit board is much smaller than the circuit board being inspected. Thus, multiple images of the circuit board are required to accomplish a complete inspection of the circuit board. FIG. 12 shows a circuit board 710 having multiple components 712 mounted thereon via connections 714. Several board views 730 are illustrated. For example, board view 730a includes components 712a and 712b and corresponding connections 714a, 714b, 714c and 714d. Board view 730b includes component 712c and its corresponding connections 714. Board view 730c includes components 712d, 712e, 712f, 712g and 712h and their corresponding connections 714. Prior to the present invention, an operator manually determined a Delta Z value for each laser surface map point 300 (see FIGS. 4a, 4b and 4c). The present invention eliminates this error prone and time consuming process.

Using the above described processes, a Delta Z value for EACH solder connection 714 on the circuit board 710 is automatically determined and stored. Using these stored Delta Z values for each solder connection 714, a Delta Z value for each board view is then calculated. For example, a simple average all of the Delta Z's for each pin in the board view may be appropriate. However, more sophisticated methods may be appropriate for some situations.

For example, it may be determined that a particular board view could be better inspected with more than one value of Delta Z, i.e., multiple cross sectional image slices. This might occur if board warpage, board thickness, etc. caused the solder pads within a board view to be located at different Z-axis elevations.

In use, after a pattern of board views for a particular circuit board have been determined, it is a straightforward matter to calculate the Delta Z for each board view using the stored data file of Delta Z values for each individual connection on the circuit board. For example, the Delta Z value for board view 730a on circuit board 710 shown in FIG. 12, is obtained by recalling the Delta Z values for connections 714a, 714b, 714c and 714d and determining their average. Similarly, the Delta Z value for board view 730d is obtained by recalling the Delta Z values for all of the connections 714 included on components 712d, 712e, 712f, 712g and 712h and determining their average. In some situations, it may be determined that not all of the connection 714 Delta Z values need to be included in the average for that particular board view.

One advantage of this approach for determining Delta Z values for a board view is apparent when the board view changes. Previously, a change of board views required reinterpolation of the triangular mesh 318. Using the present invention, the Delta Z for the newly defined board view is readily determined by simply recalling the Delta Z values for the connections 714 included with the newly defined board view and then determining their average.

SUMMARY, RAMIFICATIONS AND SCOPE

Accordingly, the reader will see that the present invention solves many of the specific problems encountered when inspecting solder connections on circuited boards. Particularly important is that it both removes the tedious and error prone method of manually setting laser Delta Z values, while supplying correct view Delta Z values in cases where board warpage is consistent within the surface map triangles.

Furthermore, the present invention has the additional advantages in that it is very easy to use and does not require any major modifications to the inspection equipment;

it is automatic thereby removing the subjectiveness associated with manual techniques;

it improves the accuracy of Z elevation determination;

it has the ability to handle board thickness variations;

it has the ability to improve throughput since the number of map points may be reduced for some applications;

it has the ability to model board warpage more accurately; and it is compatible with the currently used manual technique and may thus be used on an as needed basis.

Although the description above contains many specificities, these should not be construed as limiting the scope of the invention but as merely providing illustrations of some of the presently preferred embodiments of this invention. For example, alternative techniques and image parameters may be used to determine which image corresponds to the proper Z-axis location; alternative interpolation techniques may be used; alternative techniques may be used to acquire the cross sectional images; alternative laser mapping or fiducial mapping techniques may be employed; alternative methods for determining a board view Delta Z from the individual connection Delta Z values may be used; alternative methods for determining the Delta Z values for particular connections may be used; etc.

Thus, the scope of the invention should be determined by the appended claims and their legal equivalents, rather than by the foregoing description and examples given. All changes which come within the meaning and range of equivalency of the claims are to be embraced within their scope.

I claim:

1. A method of determining the Z-axis position of an electrical connection on a circuit board from cross sectional X-ray images of cutting planes of the electrical connection comprising the steps of:

determining a reference Z-axis position, $Z_{RF}$;

acquiring a first cross sectional X-ray image of a cutting plane of the electrical connection at a first Z-axis position, $Z_{RF}+\Delta Z_1$, and a second cross sectional X-ray image of a cutting plane of the electrical connection at a second Z-axis position, $Z_{RF}+Z_2$;

determining a first plurality of gradients for the first cross sectional X-ray image of a cutting plane and a second plurality of gradients for the second cross sectional X-ray image of a cutting plane;

calculating a first variance for the first plurality of gradients corresponding to the first cross sectional X-ray image of a cutting plane at the first Z-axis position, $Z_{RF}+\Delta Z_1$, and a second variance for the second plurality of gradients corresponding to the second cross sectional X-ray image of a cutting plane at the second Z-axis position, $Z_{RF}+\Delta Z_2$; and analyzing the first and second variances and deriving therefrom the Z-axis position of the electrical connection.

2. A method as defined in claim 1 wherein the reference Z-axis position is determined with a range finder.

3. A method as defined in claim 2 wherein the range finder further comprises a laser range finder.

4. A method of determining the Z-axis position of an electrical connection on a circuit board from cross sectional X-ray images of cutting planes of the electrical connection comprising the steps of:

determining a reference Z-axis position, $Z_{RF}$;

acquiring a first cross sectional X-ray image of a cutting plane of the electrical connection at a first Z-axis position, $Z_{RF}+\Delta Z_1$, a second cross sectional X-ray image of a cutting plane of the electrical connection at a second Z-axis position, $Z_{RF}+\Delta Z_2$, and a third cross sectional X-ray image of a cutting plane of the electrical connection at a third Z-axis position, $Z_{RF}+\Delta Z_3$;

determining a first plurality of gradients for the first cross sectional X-ray image of a cutting plane, a second plurality of gradients for the second cross sectional X-ray image of a cutting plane and a third plurality of gradients for the third cross sectional X-ray image of a cutting plane;

calculating a first variance for the first plurality of gradients corresponding to the first cross sectional X-ray image of a cutting plane at the first Z-axis position, $Z_{RF}+\Delta Z_1$, a second variance for the second plurality of gradients corresponding to the second cross sectional X-ray image of a cutting plane at the second Z-axis position, $Z_{RF}+\Delta Z_2$, and a third variance for the third plurality of gradients corresponding to the third cross sectional X-ray image of a cutting plane at the third Z-axis position, $Z_{RF}+\Delta Z_3$; and determining a maximum variance value derived from the first, second and third variances and selecting a corresponding Z-axis position, $Z_{RF}+\Delta Z_{MAX}$, corresponding to the maximum variance value, as the Z-axis position of the electrical connection.

5. A method as defined in claim 4 further comprising the step of determining a mathematical function which includes points which approximate the values of the first, second and third variances.

6. A method as defined in claim 5 wherein the mathematical function is a parabola.

7. A method as defined in claim 5 wherein the mathematical function is a Gaussian.

8. A method as defined in claim 4 further comprising a surface mapper for creating a surface map of the circuit board.

9. A device for inspecting electrical connections on a circuit board comprising:

means for determining a reference Z-axis position, $Z_{RF}$;

means for acquiring a first cross sectional X-ray image of a cutting plane of the electrical connection at a first Z-axis position, $Z_{RF}+\Delta Z_1$, a second cross sectional X-ray image of a cutting plane of the electrical connection at a second Z-axis position, $Z_{RF}+\Delta Z_2$, and a third cross sectional X-ray image of a cutting plane of the electrical connection at a third Z-axis position, $Z_{RF}+\Delta Z_3$;

means for determining a first plurality of gradients for the first cross sectional X-ray image of a cutting plane, a second plurality of gradients for the second cross sectional X-ray image of a cutting plane and a third plurality of gradients for the third cross sectional X-ray image of a cutting plane;

means for calculating a first variance for the first plurality of gradients corresponding to the first cross sectional X-ray image of a cutting plane at the first Z-axis position, $Z_{RF}+\Delta Z_1$, a second variance for the second plurality of gradients corresponding to the second cross sectional X-ray image of a cutting plane at the second Z-axis position, $Z_{RF}+\Delta Z_2$, and a third variance for the third plurality of gradients corresponding to the third cross sectional X-ray image of a cutting plane at the third Z-axis position, $Z_{RF}+\Delta Z_3$; and means for determining a maximum variance value derived from the first, second and third variances and selecting a corresponding Z-axis position, $Z_{RF}+\Delta Z_{MAX}$, corresponding to the maximum variance value, as the Z-axis position of the electrical connection.

10. A device as defined in claim 9 further comprising means for determining a mathematical function which includes points which approximate the values of the first, second and third variances.

11. A device as defined in claim 10 wherein the Z-axis position, $Z_{RF}+\Delta Z_{MAX}$, corresponding to the maximum variance value equals a Z-axis position which corresponds to a maximum value of the mathematical function.

12. A device as defined in claim 10 wherein the mathematical function is one of a parabola or a Gaussian.

13. A device as defined in claim 9 wherein the means for determining the reference Z-axis position further comprises a laser range finder.

14. A method for inspecting electrical connections on a circuit board comprising the steps of:

acquiring a plurality of cross sectional X-ray images of cutting planes for substantially all of the electrical connections on the circuit board;

determining a Z-axis position for substantially all of the electrical connections on the circuit board from the plurality of cross sectional X-ray images of cutting planes of the electrical connections;

storing the Z-axis positions for substantially all of the electrical connections on the circuit board in a data base;

selecting a first board view which includes a first portion of the circuit board; and deriving from the stored values of the Z-axis positions for the electrical connections included within the first board view, a Z-axis position for the first board view.

15. A method as defined in claim 14 further comprising the step of creating a surface map of the circuit board with a range finder.

16. A method as defined in claim 14 further comprising the steps of:

selecting a second board view which includes a second portion of the circuit board; and deriving from the stored values of the Z-axis positions for the electrical connections included within the second board view, a Z-axis position for the second board view.

17. A method for determining the Z-axis position of an electrical connection on a circuit board comprising the steps of:

acquiring two or more cross sectional X-ray images of cutting planes of an object, at two or more Z-axis positions of the same object, of an area of the circuit board which includes the electrical connection; and comparing and analyzing said two or more cross sectional X-ray images of cutting planes at said two or more Z-axis positions, and deriving therefrom the Z-axis position of the electrical connection.

18. A method as defined in claim 17 further comprising the step of determining a reference Z-axis position, $Z_{RF}$.

19. A method as defined in claim 18 further comprising the steps of:

acquiring a first cross sectional X-ray image of a cutting plane of the electrical connection at a first Z-axis position, $Z_{RF}+\Delta Z_1$, and a second cross sectional X-ray image of a cutting plane of the electrical connection at a second Z-axis position, $Z_{RF}+\Delta Z_2$;

determining a first plurality of gradients for the first cross sectional X-ray image of a cutting plane and a second plurality of gradients for the second cross sectional X-ray image of a cutting plane;

calculating a first variance for the first plurality of gradients corresponding to the first cross sectional X-ray image of a cutting plane at the first Z-axis position, $Z_{RF}+\Delta Z_1$, and a second variance for the second plurality of gradients corresponding to the second cross sectional X-ray image of a cutting plane at the second Z-axis position, $Z_{RF}+\Delta Z_2$; and analyzing the first and second variances and deriving therefrom the Z-axis position of the electrical connection.

20. A method as defined in claim 19 wherein the image gradients are approximated over a K×K pixel grid by the following relation:

$$G_{MR}[f(x,y)] \approx |f(x-N,y-N)-f(x+M,y+M)|+|f(x+M,y-N)-f(x-N,y+M)|$$

where f(x,y) represents a gray value of a pixel located at x,y; K is an integer which is greater than or equal to 2; N=(K−1)/2 rounded down to the nearest integer; and M=K−N−1.

21. A method as defined in claim 18 wherein the reference Z-axis position is determined with a range finder.

22. A method as defined in claim 21 wherein the range finder further comprises a laser range finder.

23. A method as defined in claim 17 further comprising the steps of:

determining a Z-axis position for substantially all of the electrical connections on the circuit board;

storing the Z-axis positions for substantially all of the electrical connections on the circuit board in a data base;

selecting a first board view which includes a first portion of the circuit board; and deriving from the stored values of the Z-axis positions for the electrical connections included within the first board view, a Z-axis position for the first board view.

24. A device for inspecting electrical connections on a circuit board comprising:

means for acquiring two or more cross sectional X-ray images of cutting planes of and object, at two or more Z-axis positions of the same object, of an area of the circuit board which includes the electrical connection; and means for comparing and analyzing said two or more cross sectional X-ray images of cutting planes at said two or more Z-axis positions, and deriving therefrom the Z-axis position of the electrical connection.

25. A device as defined in claim 24 further comprising:

means for determining a reference Z-axis position, $Z_{RF}$;

means for acquiring a first cross sectional X-ray image of a cutting plane of the electrical connection at a first Z-axis position, $Z_{RF}+\Delta Z_1$, a second cross sectional X-ray image of a cutting plane of the electrical connection at a second Z-axis position, $Z_{RF}+\Delta Z_2$, and a third cross sectional X-ray image of a cutting plane of the electrical connection at a third Z-axis position, $Z_{RF}+\Delta Z_3$;

means for determining a first plurality of gradients for the first cross sectional X-ray image of a cutting plane, a second plurality of gradients for the second cross sectional X-ray image of a cutting plane and a third plurality of gradients for the third cross sectional X-ray image of a cutting plane;

means for calculating a first variance for the first plurality of gradients corresponding to the first cross sectional X-ray image of a cutting plane at the first Z-axis position, $Z_{RF}+\Delta Z_1$, a second variance for the second plurality of gradients corresponding to the second cross sectional X-ray image of a cutting plane at the second Z-axis position, $Z_{RF}+\Delta Z_2$, and a third variance for the third plurality of gradients corresponding to the third cross sectional X-ray image of a cutting plane at the third Z-axis position, $Z_{RF}+\Delta Z_3$; and means for determining a maximum variance value derived from the first, second and third variances and selecting a corresponding Z-axis position, $Z_{RF}+Z_{MAX}$, corresponding to the maximum variance value, as the Z-axis position of the electrical connection.

26. A device as defined in claim 24 further comprising a surface mapper for creating a surface map of the circuit board.

27. A method for determining the Z-axis position of an electrical connection on a circuit board comprising the steps of:

acquiring two or more cross sectional images, at two or more Z-axis positions, of an area of the circuit board which includes the electrical connection;

comparing and analyzing said two or more cross sectional images at said two or more Z-axis positions, and deriving therefrom the Z-axis position of the electrical connection;

determining a reference Z-axis position, $Z_{RF}$;

acquiring a first cross sectional image of the electrical connection at a first Z-axis position, $Z_{RF}+\Delta Z_1$, and a second cross sectional image of the electrical connection at a second Z-axis position, $Z_{RF}+\Delta Z_2$;

determining a first plurality of gradients for the first cross sectional image and a second plurality of gradients for the second cross sectional image;

calculating a first variance for the first plurality of gradients corresponding to the first cross sectional image at the first Z-axis position $Z_{RF}+\Delta Z_1$, and a second variance for the second plurality of gradients corresponding to the second cross sectional image at the second Z-axis position $Z_{RF}+\Delta Z_2$, wherein the image gradients are approximated over a K×K pixel grid by the following relation:

$$G_{MR}[f(x,y)] \approx |f(x-N,y-N)-f(x+M,y+M)|+|f(x+M,y-N)-f(x-N,y+M)|$$

where $f(x,y)$ represents a gray value of a pixel located at x,y; K is an integer which is greater than or equal to 2; $N=(K-1)/2$ rounded down to the nearest integer; and $M=K-N-1$; and analyzing the first and second variances and deriving therefrom the Z-axis position of the electrical connection.

* * * * *